United States Patent
Talwar et al.

(10) Patent No.: US 9,212,199 B2
(45) Date of Patent: Dec. 15, 2015

(54) CATALYST COMPOUNDS

(71) Applicant: THE UNIVERSITY OF LIVERPOOL, Liverpool (GB)

(72) Inventors: Dinesh Talwar, Liverpool (GB); Weijun Tang, Liverpool (GB); Chao Wang, Liverpool (GB); Barbara Villa Marcos, Liverpool (GB); Jianliang Xiao, Liverpool (GB)

(73) Assignee: The University of Liverpool, Liverpool (GB)

( * ) Notice: Subject to any disclaimer, the term of this patent is extended or adjusted under 35 U.S.C. 154(b) by 0 days.

(21) Appl. No.: 14/394,239

(22) PCT Filed: Apr. 15, 2013

(86) PCT No.: PCT/GB2013/050959
§ 371 (c)(1),
(2) Date: Oct. 13, 2014

(87) PCT Pub. No.: WO2013/153407
PCT Pub. Date: Oct. 17, 2013

(65) Prior Publication Data
US 2015/0080592 A1  Mar. 19, 2015

(30) Foreign Application Priority Data
Apr. 13, 2012 (GB) .................... 1206572.8

(51) Int. Cl.
| C07F 15/02 | (2006.01) |
| C07F 17/02 | (2006.01) |
| C07F 15/00 | (2006.01) |
| C07B 31/00 | (2006.01) |
| B01J 31/18 | (2006.01) |
| B01J 31/22 | (2006.01) |

(52) U.S. Cl.
CPC ......... *C07F 15/0033* (2013.01); *B01J 31/1805* (2013.01); *B01J 31/2295* (2013.01); *C07B 31/00* (2013.01); *C07F 17/02* (2013.01); *B01J 2231/641* (2013.01); *B01J 2231/643* (2013.01); *B01J 2531/827* (2013.01)

(58) Field of Classification Search
CPC .. C07F 15/0033; C07F 17/02; B01J 31/2295; B01J 2231/641; B01J 2531/827; C07B 31/00
USPC ......................................... 556/137; 564/398
See application file for complete search history.

(56) References Cited

FOREIGN PATENT DOCUMENTS

WO  WO 2011/148124  1/2011

OTHER PUBLICATIONS

International Search Report for PCT/GB2013/050959, mailed on Jun. 25, 2013.
UK Search Report for GB1206572.8, completed on Jul. 19, 2012.
Wang, Chao et al., A Versatile Catalyst for Reductive Amination by Transfer Hydrogenation, Angewandte Chemie International Edition, 49 (41), 2010, 7548-7552.
Han, Ying-Feng et al., Alkyne Insertion Induced Regiospecific C-H activation with [Cp*MCl$_2$]$_2$ (M=Ir, Rh), Organometallics, 30 (4), 2011, 905-911.
Lei. Qian et al., Fast Reductive Amination by Transfer Hydrogenation "on Water", Chemistry a European Journal, 19(12), 2013, 4021-4029.

*Primary Examiner* — Porfirio Nazario Gonzalez
(74) *Attorney, Agent, or Firm* — Barnes & Thornburg LLP

(57) ABSTRACT

The present invention relates to an iridium-based catalyst compound for hydrogenating reducible moieties, especially imines and iminiums, the catalyst compounds being defined by the formulas: where ring B is either itself polycyclic, or ring B together with R is polycyclic. The catalysts of the invention are particularly effective in reductive amination procedures 10 which involve the in situ generation of the imine or iminium under reductive hydrogenative conditions.
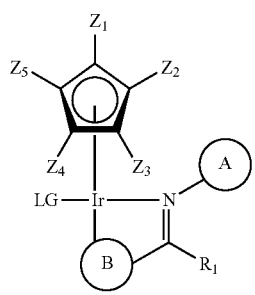
Formula I
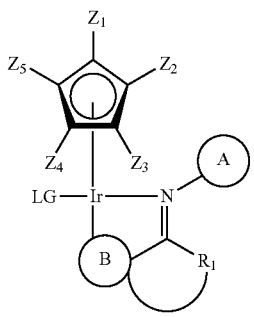
Formula A
20 Claims, 1 Drawing Sheet

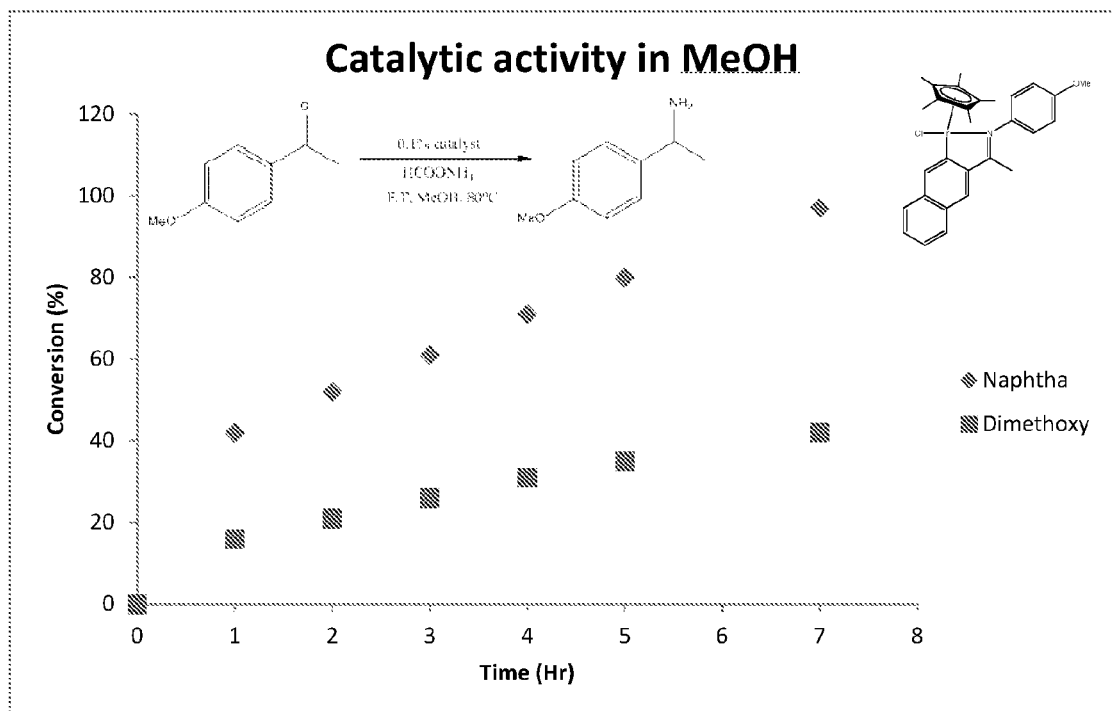

CATALYST COMPOUNDS

CROSS-REFERENCE TO RELATED APPLICATIONS

This application is a national stage entry under 35 USC §371(b) of PCT International Application No. PCT/GB2013/050959, filed Apr. 15, 2013, and claims the benefit of United Kingdom Patent Application No. 1206572.8, filed on Apr. 13, 2012, both of which are expressly incorporated by reference herein.

INTRODUCTION

The present invention relates to catalyst compounds and, more specifically, to catalyst compounds for use in the hydrogenation of reducible substrates. The invention also relates to a method for preparing these catalyst compounds, a method of reducing a reducible substrate using these compounds and to compositions comprising these catalyst compounds.

BACKGROUND

Reduction of imines and reductive amination reactions are commonly employed in the chemical field to produce amines. For instance, reductive amination reactions are widely used in the synthesis of pharmaceutical compounds and their intermediates. Typically, reductive amination of an aldehyde or ketone involves their reaction with either ammonia, a primary amine, or secondary amine under reductive conditions to respectively yield corresponding primary, secondary, or tertiary amines.

Reducing agents such as $NaBH_3CN$, $NaBH(OAc)_3$, and boranes (e.g. pyridine borane) are commonly used to provide the reductive conditions required in the reductive amination process. However, for successful reductive aminations, a significant excess of $NaBH_3CN$ is often required for the reactions to reach completion within a reasonable timeframe. $NaBH_3CN$ gives rise to slow reactions, particularly where aromatic ketones and weakly basic amines are used, and final products are often contaminated with highly toxic cyanide. Moreover, $NaBH_3CN$ is itself highly toxic and leads to the evolution of toxic byproducts such as HCN and NaCN during post-reaction workups. $NaBH(OAc)_3$ again needs to be used in excessive quantities and is poorly soluble in most commonly used organic solvents. Pyridine borane, on the other hand, can be unsafe to use on industrial scales due to its propensity to violently decompose.

More recently, certain cyclometalated Iridium complexes have been developed to address some of the problems of the prior art (Xiao J et al, *Angew. Chem. Int. Ed.,* 2010, 49: 7548-7552). However, these catalysts, though suitable for use under certain conditions, are not necessarily appropriate for all reductive amination reaction conditions. In order to meet particular synthetic requirements, reaction conditions (e.g. solvents, temperature, pH, etc.) may need to be tailored to the reagents or products of the reductive amination process rather than the catalyst. As such, it is an object of the invention to provide alternative catalysts which meet particular synthetic needs that the prior art catalysts fail to address.

SUMMARY OF THE INVENTION

The inventors have found a particular set of catalyst compounds which perform well in general, and particularly well under certain synthetically useful conditions.

In accordance with a first aspect of the present invention there is provided a catalyst compound of Formula I:

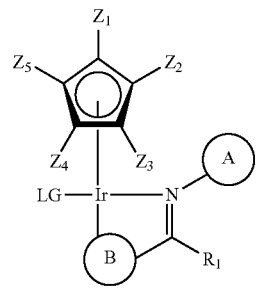

Formula I wherein:
ring A is aryl or heteroaryl, optionally substituted by one or two groups selected from hydroxyl, $NR^aR^b$, (1-6C)alkyl, (1-6C)alkoxy, or aryl which is optionally substituted by halogeno, hydroxyl, $NR^aR^b$, (1-6C)alkyl, (1-6C)alkoxy, wherein $R^a$ and $R^b$ are each independently selected from hydrogen or (1-6C)alkyl;
ring B is a bicyclic or tricyclic aromatic or heteroaromatic fused ring system, optionally substituted by one or more groups selected from halogeno, hydroxyl, $NR^cR^d$, (1-6C)alkyl, (1-6C)alkoxy, $[NR^cR^dR^e]^+$, nitro, cyano, formyl, carboxy, carbamoyl, sulphamoyl, ureido, isocyano, sulphonyl, sulphonate, trihalomethyl (e.g. trifluoromethyl), mercapto, wherein $R^c$, $R^d$, and $R^e$ are each independently selected from hydrogen or (1-6C)alkyl, or aryl (e.g. phenyl); or a group of the formula:

$L_1$-$Q_1$ 

wherein:
$L_1$ is absent or is selected from O, S, SO, $SO_2$, $N(R^f)$, C(O), $CH(OR^f)$, $C(O)N(R^f)$, $N(R^f)C(O)$, $N(R^f)C(O)N(R^g)$, $S(O)_2N(R^f)$, or $N(R^f)SO_2$, wherein $R^f$ and $R^g$ are each independently selected from hydrogen or (1-4C)alkyl; and;
$Q_1$ is (1-6C)alkyl, (2-6C)alkenyl, (2-6C)alkynyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; and wherein $Q_1$ is optionally further substituted by one or more substituents independently selected from halogeno, hydroxyl, $NR^cR^d$, $[NR^cR^dR^e]^+$, (1-6C)alkyl, (1-6C)alkoxy, nitro, cyano, formyl, carboxy, carbamoyl, ureido, isocyano, sulphonyl, sulphonate, trifluoromethyl, mercapto;
$R_1$ is selected from the group including hydrogen, (1-6C)alkyl, (2-6C)alkenyl, (2-6C)alkynyl, aryl, (3-6C)cycloalkyl, heteroaryl, or $R_1$ is (2-4C)alkylene or (2-4C)alkenylene linked to ring B to form a fused 5-, 6- or 7-membered ring, wherein $R_1$ is optionally substituted by one or more groups selected from halogeno, hydroxyl, $NR^hR^i$, (1-6C)alkyl, (1-6C)alkoxy, $[NR^hR^iR^j]^+$, nitro, cyano, formyl, carboxy, carbamoyl, sulphamoyl, ureido, isocyano, sulphonyl, sulphonate, trihalomethyl (e.g. trifluoromethyl), mercapto, wherein $R^h$, $R^i$, and $R^j$ are each independently selected from hydrogen or (1-6C)alkyl, or aryl (e.g. phenyl); or a group of the formula:

$L_2$-$Q_2$ 

wherein:
L₂ is absent or is selected from O, S, SO, SO₂, N(R$^k$), C(O), CH(OR$^k$), C(O)N(R$^k$), N(R$^k$)C(O), N(R$^k$)C(O)N(R$^l$), S(O)₂N(R$^k$), or N(R$^k$)SO₂, wherein R$^k$ and R$^l$ are each independently selected from hydrogen or (1-4C)alkyl; and;

Q₂ is (1-6C)alkyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; and wherein Q₂ is optionally further substituted by one or more substituents independently selected from halogeno, hydroxyl, NR$^m$R$^n$, [NR$^m$R$^n$R$^o$]⁺, (1-6C)alkyl, (1-6C)alkoxy, nitro, cyano, formyl, carboxy, carbamoyl, ureido, isocyano, sulphonyl, sulphonate, trifluoromethyl, mercapto, wherein R$^m$, R$^n$, and R$^o$ are each independently selected from hydrogen or (1-6C)alkyl, or aryl (e.g. phenyl);

LG is a leaving group (eg. halo, acetate);

Z₁, Z₂, Z₃, Z₄, and Z₅ are each independently selected from hydrogen, (1-6C)alkyl, or aryl, (1-6C)alkoxy, hydroxyl, or NR$^p$R$^q$, wherein R$^p$ and R$^q$ are each independently selected from hydrogen or (1-6C)alkyl, or aryl (e.g. phenyl).

In accordance with a second aspect of the present invention there is provided a method for preparing a catalyst compound of Formula I as defined herein, the method comprising:

reacting a compound of formula II:

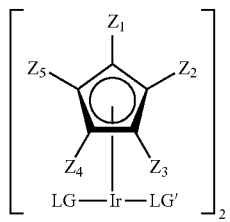

Formula II wherein Z₁, Z₂, Z₃, Z₄, Z₅, and LG are as defined herein, and LG' is a leaving group (optionally independently defined by any of the meanings given herein for LG);

with a compound of Formula III:

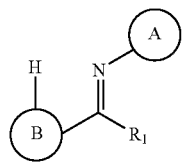

Formula III wherein ring A, ring B, and R₁ are as defined herein.

In accordance with a third aspect of the present invention there is provided a method of reducing a reducible substrate, the method comprising hydrogenating the reducible substrate in the presence of a catalyst compound of Formula I as defined herein.

In accordance with a fourth aspect of the present invention there is provided a composition comprising the catalyst compound of Formula I as defined herein.

In accordance with a fifth aspect of the present invention there is provided a kit of parts comprising the compound of Formula II as defined herein and the compound of Formula III as defined herein.

In accordance with a sixth aspect of the present invention, there is provided a catalyst compound of Formula A:

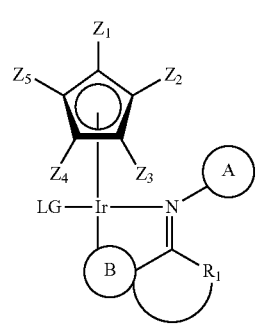

Formula A wherein:
ring A is aryl or heteroaryl, optionally substituted by one or two groups selected from hydroxyl, NR$^a$R$^b$, (1-6C)alkyl, (1-6C)alkoxy, or aryl which is optionally substituted by halogeno, hydroxyl, NR$^a$R$^b$, (1-6C)alkyl, (1-6C)alkoxy, wherein R$^a$ and R$^b$ are each independently selected from hydrogen or (1-6C)alkyl;

ring B is a aryl or heteroaryl, optionally substituted by one or more groups selected from halogeno, hydroxyl, NR$^c$R$^d$, (1-6C)alkyl, (1-6C)alkoxy, [NR$^c$R$^d$R$^e$]⁺, nitro, cyano, formyl, carboxy, carbamoyl, sulphamoyl, ureido, isocyano, sulphonyl, sulphonate, trihalomethyl (e.g. trifluoromethyl), mercapto, wherein R$^c$, R$^d$, and R$^e$ are each independently selected from hydrogen or (1-6C) alkyl, or aryl (e.g. phenyl); or a group of the formula:

L₁-Q₁ wherein:
L₁ is absent or is selected from O, S, SO, SO₂, N(R$^f$), C(O), CH(OR$^f$), C(O)N(R$^f$), N(R$^f$)C(O), N(R$^f$)C(O)N(R$^g$), S(O)₂N(R$^f$), or N(R$^f$)SO₂, wherein R$^f$ and R$^g$ are each independently selected from hydrogen or (1-4C)alkyl; and Q₁ is (1-6C)alkyl, (2-6C)alkenyl, (2-6C)alkynyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; and wherein Q₁ is optionally further substituted by one or more substituents independently selected from halogeno, hydroxyl, NR$^c$R$^d$, [NR$^c$R$^d$R$^e$]⁺, (1-6C) alkyl, (1-6C)alkoxy, nitro, cyano, formyl, carboxy, carbamoyl, ureido, isocyano, sulphonyl, sulphonate, trifluoromethyl, mercapto;

R₁ is (2-4C)alkylene or (2-4C)alkenylene linked to ring B to form a fused 5- 6-, or 7-membered ring, wherein R₁ is optionally substituted by one or more groups selected from halogeno, hydroxyl, NR$^h$R$^i$, (1-6C)alkyl, (1-6C) alkoxy, [NR$^h$R$^i$R$^j$]⁺, nitro, cyano, formyl, carboxy, carbamoyl, sulphamoyl, ureido, isocyano, sulphonyl, sulphonate, trihalomethyl (e.g. trifluoromethyl), mercapto, wherein R$^h$, R$^i$, and R$^j$ are each independently selected from hydrogen or (1-6C)alkyl, or aryl (e.g. phenyl); or a group of the formula:

L₂-Q₂ wherein:
L₂ is absent or is selected from O, S, SO, SO₂, N(R$^k$), C(O), CH(OR$^k$), C(O)N(R$^k$), N(R$^k$)C(O), N(R$^k$)C(O)

N(R$^j$), S(O)$_2$N(R$^k$), or N(R$^k$)SO$_2$, wherein R$^k$ and R$^l$ are each independently selected from hydrogen or (1-4C)alkyl; and;

Q$_2$ is (1-6C)alkyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; and wherein Q$_2$ is optionally further substituted by one or more substituents independently selected from halogeno, hydroxyl, NR$^m$R$^n$, [NR$^m$R$^n$R$^o$]$^+$, (1-6C)alkyl, (1-6C)alkoxy, nitro, cyano, formyl, carboxy, carbamoyl, ureido, isocyano, sulphonyl, sulphonate, trifluoromethyl, mercapto, wherein R$^m$, R$^n$, and R$^o$ are each independently selected from hydrogen or (1-6C)alkyl, or aryl (e.g. phenyl);

LG is a leaving group (eg. halo, acetate);

Z$_1$, Z$_2$, Z$_3$, Z$_4$, and Z$_5$ are each independently selected from hydrogen, (1-6C)alkyl, or aryl, (1-6C)alkoxy, hydroxyl, or NR$^p$R$^q$, wherein R$^p$ and R$^q$ are each independently selected from hydrogen or (1-6C)alkyl, or aryl (e.g. phenyl).

In accordance with a seventh aspect of the present invention there is provided a method for preparing a catalyst compound of Formula A as defined herein, the method comprising:

reacting a compound of formula II:

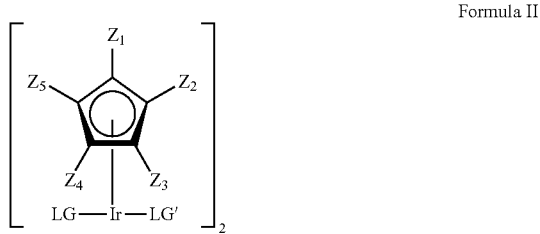

Formula II wherein Z$_1$, Z$_2$, Z$_3$, Z$_4$, Z$_5$, and LG are as defined herein, and LG' is a leaving group (optionally independently defined by any of the meanings given herein for LG);

with a compound of Formula B:

Formula B wherein ring A, ring B, and R$_1$ are as defined herein.

In accordance with an eighth aspect of the present invention there is provided a method of reducing a reducible substrate, the method comprising hydrogenating the reducible substrate in the presence of a catalyst compound of Formula A as defined herein.

In accordance with a ninth aspect of the present invention there is provided a composition comprising the catalyst compound of Formula A as defined herein.

In accordance with a tenth aspect of the present invention there is provided a kit of parts comprising the compound of Formula II as defined herein and the compound of Formula B as defined herein.

Any features, including optional, suitable, and preferred features, described in relation to any particular aspect of the invention may also be features, including optional, suitable and preferred features, of any other aspect of the present invention. In particular, the definitions for Ring A, Ring B, R$_1$, Z$_1$, Z$_2$, Z$_3$, Z$_4$, Z$_5$, LG, and LG' used in relation to compounds of Formulas I and III are also, unless stated otherwise, applicable definitions in relation to compounds of Formulas A and B.

BRIEF DESCRIPTION OF THE DRAWINGS

For a better understanding of the invention, and to show how embodiments of the same are put into effect, reference is now made, by way of example, to the following diagrammatic drawings, in which:

FIG. 1 is a graph showing a comparison of the catalytic activity of catalyst compounds 2b (prior art compound—solid squares) and 2c (compound of the invention—solid diamonds) in the illustrated reductive amination in MeOH.

DETAILED DESCRIPTION OF THE INVENTION

Definitions

Unless otherwise stated, the following terms used in the specification and claims have the following meanings set out below.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

An "alkylene" or "alkenylene," group is respectively an alkyl or alkenyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene, and the like.

"(2-6C)alkenylene" means a linear divalent hydrocarbon radical of two to six carbon atoms or a branched divalent hydrocarbon radical of three to six carbon atoms, containing at least one double bond, for example, as in ethenylene, 2,4-pentadienylene, and the like.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicyclo[2.2.1]heptyl.

"(3-8C)cycloalkenyl" means a hydrocarbon ring containing at least one double bond, for example, cyclobutenyl, cyclopentenyl, cyclohexenyl or cycloheptenyl, such as 3-cyclohexen-1-yl, or cyclooctenyl.

"(3-8C)cycloalkyl-(1-6C)alkylene" means a (3-8C)cycloalkyl group covalently attached to a (1-6C)alkylene group, both of which are defined herein.

The term "halo" or "halogeno" refers to fluoro, chloro, bromo and iodo.

The term "heterocyclyl", "heterocyclic" or "heterocycle" means a non-aromatic saturated or partially saturated monocyclic, fused, bridged, or spiro bicyclic heterocyclic ring system(s). The term heterocyclyl includes both monovalent species and divalent species. Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example Advanced Organic Chemistry, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

"Heterocyclyl(1-6C)alkyl" means a heterocyclyl group covalently attached to a (1-6C)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzothienyl, dihydrobenzofuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:
a benzene ring fused to a 5- or 6-membered ring containing 1, 2 or 3 ring heteroatoms;
a pyridine ring fused to a 5- or 6-membered ring containing 1, 2 or 3 ring heteroatoms;
a pyrimidine ring fused to a 5- or 6-membered ring containing 1 or 2 ring heteroatoms;
a pyrrole ring fused to a 5- or 6-membered ring containing 1, 2 or 3 ring heteroatoms;
a pyrazole ring fused to a 5- or 6-membered ring containing 1 or 2 ring heteroatoms;
a pyrazine ring fused to a 5- or 6-membered ring containing 1 or 2 ring heteroatoms;
an imidazole ring fused to a 5- or 6-membered ring containing 1 or 2 ring heteroatoms;
an oxazole ring fused to a 5- or 6-membered ring containing 1 or 2 ring heteroatoms;
an isoxazole ring fused to a 5- or 6-membered ring containing 1 or 2 ring heteroatoms;

a thiazole ring fused to a 5- or 6-membered ring containing 1 or 2 ring heteroatoms;

an isothiazole ring fused to a 5- or 6-membered ring containing 1 or 2 ring heteroatoms;

a thiophene ring fused to a 5- or 6-membered ring containing 1, 2 or 3 ring heteroatoms;

a furan ring fused to a 5- or 6-membered ring containing 1, 2 or 3 ring heteroatoms;

a cyclohexyl ring fused to a 5- or 6-membered heteroaromatic ring containing 1, 2 or 3 ring heteroatoms; and a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

The term "linear fused ring system" and "kinked fused ring system" are used herein to describe systems comprising three or more fused rings which are respectively ortho-fused in either a linear fashion (e.g. anthracene) or a kinked fashion (e.g. phenanthrene).

"Heteroaryl(1-6C)alkyl" means a heteroaryl group covalently attached to a (1-6C)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(1-6C)alkyl" means an aryl group covalently attached to a (1-6C)alkylene group, both of which are defined herein. Examples of aryl-(1-6C)alkyl groups include benzyl, phenylethyl, and the like This specification also makes use of several composite terms to describe groups comprising more than one functionality. Such terms will be understood by a person skilled in the art. For example heterocyclyl(m-nC)alkyl comprises (m-nC) alkyl substituted by heterocyclyl.

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

Herein, use of the term "ketone" may also encompass aldehydes, though in some embodiments, the term "ketone" may be used in a manner which excludes aldehydes.

When referring to substituent positions (e.g. ortho-, para-, etc.) in relation to Ring A, said positions are suitably relative to the imine nitrogen atom to which ring A is attached in the catalyst compound, or to the corresponding amine nitrogen atom to which ring A is attached in the precursor amine compound.

When referring to substituent positions (e.g. ortho-, para-, etc.) in relation to Ring B, said positions are suitably relative to the imine carbon atom to which ring B is attached in the catalyst compound, or to the corresponding carbonyl carbon atom to which ring B is attached in the precursor carbonyl compound.

The terms "electron withdrawing group" and "electron donating group" are well understood by those skilled in the art, and herein refer to particular substituent groups which respectively withdraw or donate electron density from or to a correspondingly substituted π-bonding system, such as a phenyl group. Electron donating substituents are determinable by a number of methods, including by reference to substituent constants in accordance with the Hammett equation or other equivalent mathematical and experimental techniques. Electron donation is measured relative to hydrogen, and a substituent may be said to be electron donating where it contributes more electron density to the π-bonding system than a standard hydrogen substituent. Electron withdrawing substituents are the opposite of electron donating groups, and a substituent may be said to be electron withdrawing where it withdraws more electron density from the π-bonding system than a standard hydrogen substituent.

Herein, a particular substituent group (e.g. a nitro group) is considered to be "in π-conjugation with" another group (e.g. an imine group) where p- or π-orbitals of the particular substituent group are electronically linked to p- or π-orbitals of the other group, optionally via an intervening π-system (e.g. such as an alkene, phenyl, or naphthyl moiety). By way of example, in the molecule depicted below, the nitro group, denoted by #, is in π-conjugation with the imine, whose carbon is denoted by *, via an intervening naphthyl π-system.

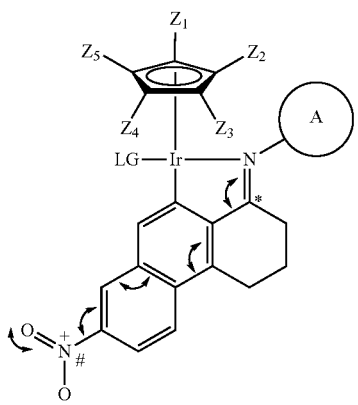

References herein to the catalyst compound or "compound of the invention" may refer to any enantiomer, a mixture of enantiomers, or a racemic mixture of enantiomers.

The phrase "compound of the invention" means those compounds which are disclosed herein, both generically and specifically.

Catalyst Compounds

In accordance with a first aspect of the present invention there is provided a catalyst compound of Formula I:

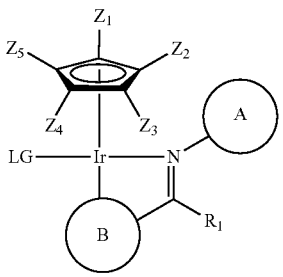

Formula I wherein ring A, ring B, $R_1$, LG, $Z_1$, $Z_2$, $Z_3$, $Z_4$, and $Z_5$ are as defined hereinbefore.

In a particular embodiment, the catalyst compound is defined by Formula I:

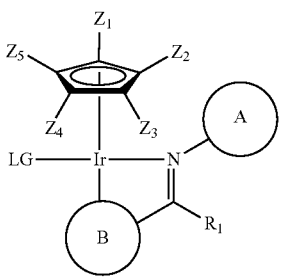

Formula I wherein:
ring A is aryl or heteroaryl, substituted by one or two groups selected from hydroxyl, $NR^aR^b$, (1-6C)alkyl, (1-6C)alkoxy, or aryl which is optionally substituted by halogeno, hydroxyl, $NR^aR^b$, (1-6C)alkyl, (1-6C)alkoxy, wherein $R^a$ and $R^b$ are each independently selected from hydrogen or (1-6C)alkyl;

ring B is a bicyclic or tricyclic aromatic or heteroaromatic fused ring system, optionally substituted by one or more groups selected from halogeno, hydroxyl, $NR^cR^d$, (1-6C)alkyl, (1-6C)alkoxy, $[NR^cR^dR^e]^+$, nitro, cyano, formyl, carboxy, carbamoyl, sulphamoyl, ureido, isocyano, sulphonyl, sulphonate, trihalomethyl (e.g. trifluoromethyl), mercapto, wherein $R^c$, $R^d$, and $R^e$ are each independently selected from hydrogen or (1-6C)alkyl, or aryl (e.g. phenyl); or a group of the formula:

$L_1$-$Q_1$ wherein:
$L_1$ is absent or is selected from O, S, SO, $SO_2$, $N(R^f)$, C(O), $CH(OR^f)$, $C(O)N(R^f)$, $N(R^f)C(O)$, $N(R^f)C(O)N(R^g)$, $S(O)_2N(R^f)$, or $N(R^f)SO_2$, wherein $R^f$ and $R^g$ are each independently selected from hydrogen or (1-4C)alkyl; and;

$Q_1$ is (1-6C)alkyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; and wherein $Q_1$ is optionally further substituted by one or more substituents independently selected from halogeno, hydroxyl, $NR^cR^d$, $[NR^cR^dR^e]^+$, (1-6C)alkyl, (1-6C)alkoxy, nitro, cyano, formyl, carboxy, carbamoyl, ureido, isocyano, sulphonyl, sulphonate, trifluoromethyl, mercapto;

$R_1$ is selected from the group including hydrogen, (1-6C)alkyl, (2-6C)alkenyl, (2-6C)alkynyl, aryl, (3-6C)cycloalkyl, heteroaryl, or $R_1$ is (2-3C)alkylene or (2-3C)alkenylene linked to ring B to form a fused 5- or 6-membered ring, wherein $R_1$ is optionally substituted by one or more groups selected from halogeno, hydroxyl, $NR^hR^i$, (1-6C)alkyl, (1-6C)alkoxy, $[NR^hR^iR^j]^+$, nitro, cyano, formyl, carboxy, carbamoyl, sulphamoyl, ureido, isocyano, sulphonyl, sulphonate, trihalomethyl (e.g. trifluoromethyl), mercapto, wherein $R^h$, $R^i$, and $R^j$ are each independently selected from hydrogen or (1-6C)alkyl, or aryl (e.g. phenyl); or a group of the formula:

$L_2$-$Q_2$ wherein:
$L_2$ is absent or is selected from O, S, SO, $SO_2$, $N(R^k)$, C(O), $CH(OR^k)$, $C(O)N(R^k)$, $N(R^k)C(O)$, $N(R^k)C(O)N(R^l)$, $S(O)_2N(R^k)$, or $N(R^k)SO_2$, wherein $R^k$ and $R^l$ are each independently selected from hydrogen or (1-4C)alkyl; and;

$Q_2$ is (1-6C)alkyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; and wherein $Q_2$ is optionally further substituted by one or more substituents independently selected from halogeno, hydroxyl, $NR^mR^n$, $[NR^mR^nR^o]^+$, (1-6C)alkyl, (1-6C)alkoxy, nitro, cyano, formyl, carboxy, carbamoyl, ureido, isocyano, sulphonyl, sulphonate, trifluoromethyl, mercapto, wherein $R^m$, $R^n$, and $R^o$ are each independently selected from hydrogen or (1-6C)alkyl, or aryl (e.g. phenyl);

LG is a leaving group (eg. halo, acetate);
$Z_1$, $Z_2$, $Z_3$, $Z_4$, and $Z_5$ are each independently selected from hydrogen, (1-6C)alkyl, or aryl.

Particular catalyst compounds of the present invention include, for example, compounds of Formula I, wherein, unless otherwise stated, each of ring A, ring B, $R_1$, LG, $Z_1$, $Z_2$, $Z_3$, $Z_4$, and $Z_5$ has any one of the meanings defined hereinbefore or in any of paragraphs (1) to (33) hereinafter:—

(1) Ring A is aryl, optionally substituted by one or two groups selected from hydroxyl, $NR^aR^b$, (1-6C)alkyl, (1-6C)alkoxy, or aryl which is optionally substituted by halogeno, hydroxyl, $NR^aR^b$, (1-6C)alkyl, (1-6C)alkoxy, wherein $R^a$ and $R^b$ are each independently selected from hydrogen or (1-6C)alkyl.

(2) Ring A is phenyl, optionally substituted by one or two groups selected from hydroxyl, $NR^aR^b$, (1-3C)alkyl, (1-3C)alkoxy, or aryl which is optionally substituted by halogeno, hydroxyl, $NR^aR^b$, (1-3C)alkyl, (1-3C)alkoxy, wherein $R^a$ and $R^b$ are each independently selected from hydrogen or (1-2C)alkyl.

(3) Ring A is phenyl, optionally substituted, in either or both of the ortho- and/or para-position relative to the imine nitrogen atom to which ring A is attached, by one or two groups selected from hydroxyl, $NR^aR^b$, (1-3C)alkyl, (1-3C)alkoxy, or aryl which is optionally substituted by halogeno, hydroxyl, $NR^aR^b$, (1-3C)alkyl, (1-3C)alkoxy, wherein $R^a$ and $R^b$ are each independently selected from hydrogen or (1-2C)alkyl.

(4) Ring A is phenyl substituted by one or two (1-3C) alkoxy groups.

(5) Ring A is phenyl substituted by one or two (1-3C) alkoxy groups in either or both of the ortho- and/or para-position relative to the imine nitrogen atom to which ring A is attached.

(6) Ring A is phenyl substituted by one (1-3C)alkoxy group in either the ortho- or para-position relative to the imine nitrogen atom to which ring A is attached.
(7) Ring A is para-methoxyphenyl.
(8) Any bicyclic fused ring systems of Ring B are ortho-fused.
(9) Any tricyclic fused ring systems of Ring B are solely ortho-fused.
(10) Any tricyclic fused ring systems of Ring B are ortho- and peri-fused.
(11) Any tricyclic fused ring systems of Ring B are linear fused ring systems (i.e. as opposed to kinked fused ring systems).
(12) ring B is a bicyclic aromatic fused ring system, optionally substituted by one or more groups selected from halogeno, hydroxyl, $NR^cR^d$, (1-3C)alkyl, (1-3C)alkoxy, $[NR^cR^dR^e]^+$, nitro, cyano, formyl, carboxy, carbamoyl, sulphamoyl, ureido, isocyano, sulphonyl, sulphonate, trihalomethyl (e.g. trifluoromethyl), mercapto, wherein $R^c$, $R^d$, and $R^e$ are each independently selected from hydrogen or (1-3C)alkyl, or aryl (e.g. phenyl); or a group of the formula:

$L_1$-$Q_1$ wherein:
$L_1$ is absent or is selected from O, S, SO, $SO_2$, $N(R^f)$, C(O), $CH(OR^f)$, $C(O)N(R^f)$, $N(R^f)C(O)$, $N(R^f)C(O)N(R^g)$, $S(O)_2N(R^f)$, or $N(R^f)SO_2$, wherein $R^f$ and $R^g$ are each independently selected from hydrogen or (1-2C)alkyl; and;
$Q_1$ is (1-6C)alkyl, (2-3C)alkenyl, (1-3)alkynyl, aryl, aryl-(1-3C)alkyl, (5-6C)cycloalkyl, (5-6C)cycloalkyl-(1-3C)alkyl, (5-6C)cycloalkenyl, (5-6C)cycloalkenyl-(3-6C)alkyl, heteroaryl, heteroaryl-(1-3C)alkyl, heterocyclyl or heterocyclyl-(1-3C)alkyl; and wherein $Q_1$ is optionally further substituted by one or more substituents independently selected from halogeno, hydroxyl, $NR^cR^d$, $[NR^cR^dR^e]^+$, (1-3C)alkyl, (1-3C)alkoxy, nitro, cyano, formyl, carboxy, carbamoyl, ureido, isocyano, sulphonyl, sulphonate, trifluoromethyl, mercapto.

(13) Ring B is optionally substituted by one or more groups selected from halogeno, $[NR^cR^dR^e]^+$, nitro, cyano, formyl, carboxy, carbamoyl, sulphamoyl, ureido, isocyano, sulphonyl, sulphonate, trihalomethyl (e.g. trifluoromethyl), wherein $R^c$, $R^d$, and $R^e$ are each independently selected from hydrogen or (1-6C)alkyl, or aryl (e.g. phenyl); or a group of the formula:

$L_1$-$Q_1$ wherein:
$L_1$ is absent or is selected from SO, $SO_2$, C(O); and
$Q_1$ is (1-6C)alkyl, (2-6C)alkenyl, (2-6C)alkynyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; and wherein $Q_1$ is optionally further substituted by one or more substituents independently selected from halogeno, hydroxyl, $NR^cR^d$, $[NR^cR^dR^e]^+$, (1-6C)alkyl, (1-6C)alkoxy, nitro, cyano, formyl, carboxy, carbamoyl, ureido, isocyano, sulphonyl, sulphonate, trifluoromethyl, mercapto

(14) Ring B is optionally substituted by one or more groups selected from halogeno, $[NR^cR^dR^e]^+$, nitro, cyano, formyl, carboxy, carbamoyl, sulphamoyl, ureido, isocyano, sulphonyl, sulphonate, trihalomethyl (e.g. trifluoromethyl), wherein $R^c$, $R^d$, and $R^e$ are each independently selected from hydrogen or (1-6C)alkyl.

(15) Ring B is optionally substituted by electron withdrawing groups only (where "electron withdrawing" refers to an overall withdrawal of electron density from the fused ring system, as would be understood by the skilled person).
(16) Ring B is unsubstituted.
(17) Ring B is naphthyl, optionally substituted as defined hereinbefore in relation to Ring B.
(18) Ring B is naphthyl, optionally substituted by one or more groups selected from nitro, cyano, formyl, carboxy, carbamoyl, ureido, isocyano, sulphonyl, sulphonate, or trifluoromethyl.
(19) Ring B is naphthyl.
(20) Ring B is β,β-naphthyl, optionally substituted as herein defined in relation to Ring B, such that the naphthyl substituent is attached to the iridium atom and imine-carbon atom respectively at the 2- and 3-position of the naphthyl ring, i.e. has the connectivity:

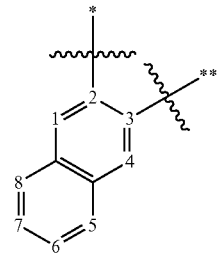

wherein * represents the point of attachment to the iridium atom of the catalyst compound, and wherein ** represent the point of attachment to the imine-carbon atom to which the B ring is attached.

(21) $R_1$ is selected from the group including hydrogen or (1-6C)alkyl, or $R_1$ is (2-4C)alkylene or (2-4C)alkenylene linked to ring B to form a fused 5-, 6-, or 7-membered ring, wherein $R_1$ is optionally substituted as herein defined.
(22) $R_1$ is selected from the group including hydrogen or (1-3C)alkyl, or $R_1$ is (2-4C)alkylene or (2-4C)alkenylene linked to ring B to form a fused 5-, 6- or 7-membered ring, wherein $R_1$ is optionally substituted by one or more groups selected from halogeno, hydroxyl, $NR^hR^i$, (1-6C)alkyl, (1-6C)alkoxy, $[NR^hR^iR^j]^+$, nitro, cyano, formyl, carboxy, carbamoyl, sulphamoyl, ureido, isocyano, sulphonyl, sulphonate, trihalomethyl (e.g. trifluoromethyl), mercapto, wherein $R^h$, $R^i$, and $R^j$ are each independently selected from hydrogen or (1-6C)alkyl, or aryl (e.g. phenyl); or a group of the formula:

$L_2$-$Q_2$ wherein:
$L_2$ is absent or is selected from O, S, SO, $SO_2$, $N(R^k)$, C(O), $CH(OR^k)$, $C(O)N(R^k)$, $N(R^k)C(O)$, $N(R^k)C(O)N(R^l)$, $S(O)_2N(R^k)$, or $N(R^k)SO_2$, wherein $R^k$ and $R^l$ are each independently selected from hydrogen or (1-4C)alkyl; and;
$Q_2$ is (1-6C)alkyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; and wherein $Q_2$ is optionally further substituted by one or more substituents independently selected from halogeno, hydroxyl, NR'''R'', [NR'''R''R°]⁺, (1-6C)alkyl, (1-6C)alkoxy, nitro, cyano, formyl, carboxy, carbamoyl, ureido, isocyano, sulphonyl, sulphonate, trifluoromethyl, mercapto, wherein R''', R'', and R° are each independently selected from hydrogen or (1-6C)alkyl, or aryl (e.g. phenyl).

(23) $R_1$ is (2-4C)alkylene linked to ring B to form a fused 5-, 6-, or 7-membered ring, optionally substituted as defined herein.

(24) $R_1$ is selected from the group including hydrogen or methyl, or $R_1$ is (3C)alkylene linked to ring B to form a fused 6-membered ring.

(25) $R_1$ is methyl.

(26) LG is halogeno (e.g. chloro, bromo, iodo), carboxylate (e.g. acetate, trifluoroacetate), sulfonate (e.g. triflate, tosylate, mesylate), nitrate, phosphate, phenolate.

(27) LG is halogeno (e.g. chloro, bromo, iodo), or carboxylate (e.g. acetate, trifluoroacetate).

(28) LG is chloro.

(29) $Z_1, Z_2, Z_3, Z_4$, and $Z_5$ are each independently selected from hydrogen, (1-6C)alkyl, phenyl, (1-3C)alkoxy, hydroxyl, or $NR^pR^q$, wherein $R^p$ and $R^q$ are each independently selected from hydrogen or (1-6C)alkyl, or aryl (e.g. phenyl).

(30) $Z_1, Z_2, Z_3, Z_4$, and $Z_5$ are each independently selected from hydrogen, (1-6C)alkyl, or phenyl.

(31) $Z_1, Z_2, Z_3, Z_4$, and $Z_5$ are each independently selected from hydrogen or methyl.

(32) $Z_1, Z_2, Z_3, Z_4$, and $Z_5$ are all hydrogen or methyl.

(33) $Z_1, Z_2, Z_3, Z_4$, and $Z_5$ are all methyl.

Where ring B is naphthyl, whether further substituted or otherwise it may be attached to the iridium and imine-carbon atoms respectively as either α,β-naphthyl, β,β-naphthyl, or β,α-naphthyl, though most suitably the naphthyl is β,β-naphthyl. In naphthalene there are two sets of equivalent hydrogen atoms: the alpha (α) positions are positions 1, 4, 5, and 8 on the drawing below, and the beta (β) positions are positions 2, 3, 6, and 7.

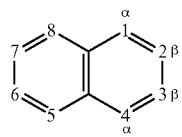

As such, β,β-naphthyl refers to a particular connectivity of the naphthyl group whereby it is attached to the iridium atom and imine-carbon atom respectively at the 2- and 3-positions. Further optional substituents, as defined herein, may be present in any of the remaining 1, 4, 5, 6, 7, or 8-positions.

In a particular group of compounds of the invention, Ring B is β,β-naphthyl optionally substituted as defined hereinbefore, i.e. the compounds have the structural formula Ia shown below:

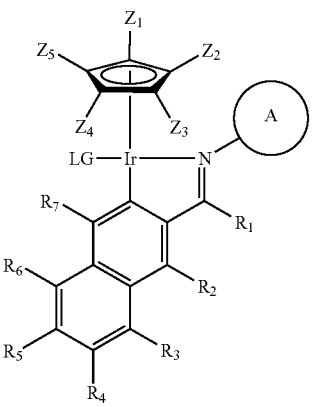

Formula Ia wherein ring A, $R_1$, $Z_1$, $Z_2$, $Z_3$, $Z_4$, $Z_5$, and LG are as defined herein, and $R_2$, $R_3$, $R_4$, $R_5$, $R_6$, and $R_7$ are each independently selected from hydrogen or any of the optional substituents for ring B defined herein.

In a particular group of compounds of the invention, Ring B is β,β-naphthyl optionally substituted as defined hereinbefore, and Ring A is phenyl optionally substituted as shown, i.e. the compounds have the structural formula Ib shown below:

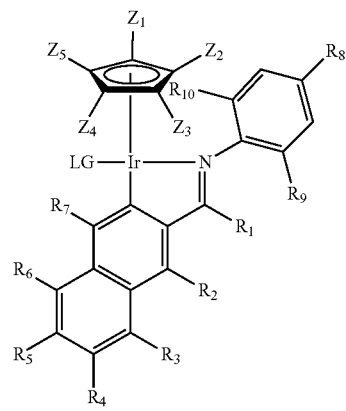

Formula Ib wherein $R_1$, $Z_1$, $Z_2$, $Z_3$, $Z_4$, $Z_5$, and LG are as defined herein, $R_2$, $R_3$, $R_4$, $R_5$, $R_6$, and $R_7$ are each independently selected from hydrogen or any of the optional substituents for ring B defined herein, and at least one of $R_8$, $R_9$, and $R_{10}$ are hydrogen, and the others of $R_8$, $R_9$, and $R_{10}$ are each independently selected from hydrogen or any of the optional substituents for ring A defined herein. In a particular embodiment, one or two of $R_8$, $R_9$, and $R_{10}$ are methoxy. In a particular embodiment, $R_8$ is methoxy and $R_9$ and $R_{10}$ are both hydrogen.

In a particular group of compounds of the invention, Ring B is β,β-naphthyl, and Ring A is phenyl optionally substituted as shown, $Z_1, Z_2, Z_3, Z_4$, and $Z_5$ are all methyl, i.e. the compounds have the structural formula Ic shown below:

Formula Ic

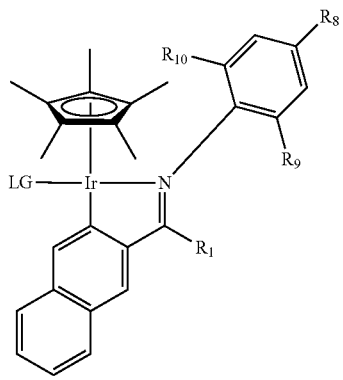

wherein $R_1$ and LG are as defined herein, at least one of $R_8$, $R_9$, and $R_{10}$ is hydrogen, and the others of $R_8$, $R_9$, and $R_{10}$ are each independently selected from hydrogen or any of the optional substituents for ring A defined herein. In a particular embodiment, one or two of $R_8$, $R_9$, and $R_{10}$ are methoxy. In a particular embodiment, $R_8$ is methoxy and $R_9$ and $R_{10}$ are both hydrogen.

In a particular embodiment, the catalyst compound has the structural formula:

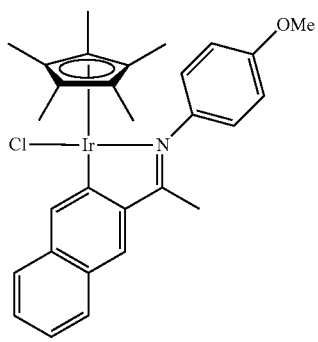

In a particular group of compounds of the invention, the catalyst compound is selected from any one of:

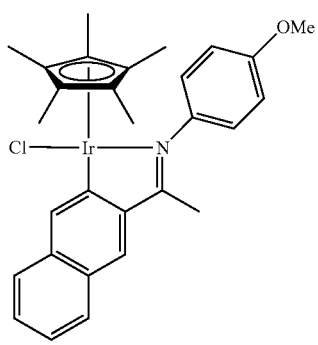

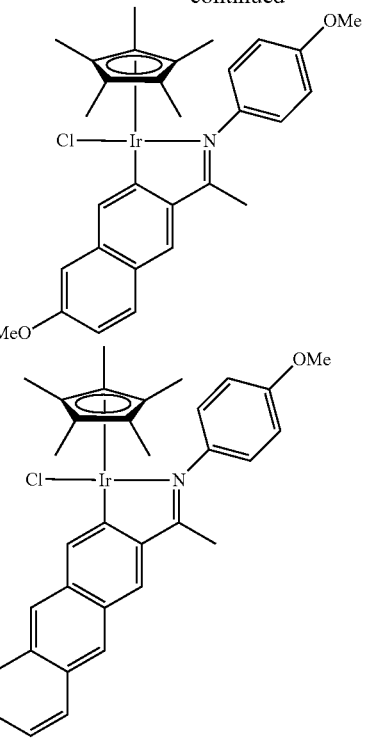

In accordance with a sixth aspect of the present invention, there is provided a catalyst compound of Formula A:

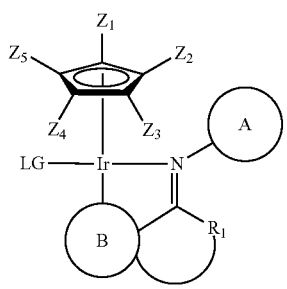

Formula A wherein ring A, ring B, $R_1$, LG, $Z_1$, $Z_2$, $Z_3$, $Z_4$, and $Z_5$ are as defined hereinbefore.

In a particular embodiment, the catalyst compound is defined by Formula A:

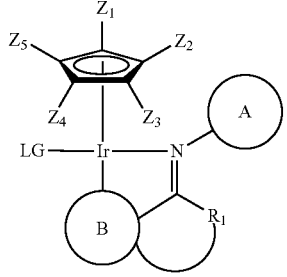

Formula A wherein:
ring A is aryl or heteroaryl, substituted by one or two groups selected from hydroxyl, $NR^aR^b$, (1-6C)alkyl, (1-6C)alkoxy, or aryl which is optionally substituted by halogeno, hydroxyl, $NR^aR^b$, (1-6C)alkyl, (1-6C)alkoxy, wherein $R^a$ and $R^b$ are each independently selected from hydrogen or (1-6C)alkyl;

ring B is a aryl or heteroaryl, optionally substituted by one or more groups selected from halogeno, hydroxyl, $NR^cR^d$, (1-6C)alkyl, (1-6C)alkoxy, $[NR^cR^dR^e]^+$, nitro, cyano, formyl, carboxy, carbamoyl, sulphamoyl, ureido, isocyano, sulphonyl, sulphonate, trihalomethyl (e.g. trifluoromethyl), mercapto, wherein $R^c$, $R^d$, and $R^e$ are each independently selected from hydrogen or (1-6C) alkyl, or aryl (e.g. phenyl); or a group of the formula:

$L_1$-$Q_1$ wherein:
$L_1$ is absent or is selected from O, S, SO, $SO_2$, $N(R^f)$, C(O), $CH(OR^f)$, $C(O)N(R^f)$, $N(R^f)C(O)$, $N(R^f)C(O)N(R^g)$, $S(O)_2N(R^f)$, or $N(R^f)SO_2$, wherein $R^f$ and $R^g$ are each independently selected from hydrogen or (1-4C)alkyl; and;

$Q_1$ is (1-6C)alkyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; and wherein $Q_1$ is optionally further substituted by one or more substituents independently selected from halogeno, hydroxyl, $NR^cR^d$, $[NR^cR^dR^e]^+$, (1-6C)alkyl, (1-6C)alkoxy, nitro, cyano, formyl, carboxy, carbamoyl, ureido, isocyano, sulphonyl, sulphonate, trifluoromethyl, mercapto;

$R_1$ is (2-4C)alkylene or (2-4C)alkenylene linked to ring B to form a fused 5- or 6- or 7-membered ring, wherein $R_1$ is optionally substituted by one or more groups selected from halogeno, hydroxyl, $NR^hR^i$, (1-6C)alkyl, (1-6C)alkoxy, $[NR^hR^iR^j]^+$, nitro, cyano, formyl, carboxy, carbamoyl, sulphamoyl, ureido, isocyano, sulphonyl, sulphonate, trihalomethyl (e.g. trifluoromethyl), mercapto, wherein $R^h$, $R^i$, and $R^j$ are each independently selected from hydrogen or (1-6C)alkyl, or aryl (e.g. phenyl); or a group of the formula:

$L_2$-$Q_2$ wherein:
$L_2$ is absent or is selected from O, S, SO, $SO_2$, $N(R^k)$, C(O), $CH(OR^k)$, $C(O)N(R^k)$, $N(R^k)C(O)$, $N(R^k)C(O)N(R^l)$, $S(O)_2N(R^k)$, or $N(R^k)SO_2$, wherein $R^k$ and $R^l$ are each independently selected from hydrogen or (1-4C)alkyl; and;

$Q_2$ is (1-6C)alkyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; and wherein $Q_2$ is optionally further substituted by one or more substituents independently selected from halogeno, hydroxyl, $NR^mR^n$, $[NR^mR^nR^o]^+$, (1-6C)alkyl, (1-6C)alkoxy, nitro, cyano, formyl, carboxy, carbamoyl, ureido, isocyano, sulphonyl, sulphonate, trifluoromethyl, mercapto, wherein $R^m$, $R^n$, and $R^o$ are each independently selected from hydrogen or (1-6C)alkyl, or aryl (e.g. phenyl);

LG is a leaving group (eg. halo, acetate);
$Z_1$, $Z_2$, $Z_3$, $Z_4$, and $Z_5$ are each independently selected from hydrogen, (1-6C)alkyl, or aryl.

Particular catalyst compounds of the present invention include, for example, compounds of Formula A, wherein, unless otherwise stated, each of ring A, ring B, $R_1$, LG, $Z_1$, $Z_2$, $Z_3$, $Z_4$, and $Z_5$ has any one of the meanings defined hereinbefore in relation to the compounds of either Formula A or Formula I (with the exception of $R_1$ whose meanings are defined in relation to Formula A only), or in any of paragraphs (34) to (40) hereinafter:—

(34) Ring A is para-methoxyphenyl.

(35) Ring B is phenyl, optionally substituted by one or more groups selected from halogeno, hydroxyl, $NR^cR^d$, (1-6C)alkyl, (1-6C)alkoxy, $[NR^cR^dR^e]^+$, nitro, cyano, formyl, carboxy, carbamoyl, sulphamoyl, ureido, isocyano, sulphonyl, sulphonate, trihalomethyl (e.g. trifluoromethyl), mercapto, wherein $R^c$, $R^d$, and $R^e$ are each independently selected from hydrogen or (1-6C)alkyl, or aryl (e.g. phenyl); or a group of the formula:

$L_1$-$Q_1$ wherein:
$L_1$ is absent or is selected from O, S, SO, $SO_2$, $N(R^f)$, C(O), $CH(OR^f)$, $C(O)N(R^f)$, $N(R^f)C(O)$, $N(R^f)C(O)N(R^g)$, $S(O)_2N(R^f)$, or $N(R^f)SO_2$, wherein $R^f$ and $R^g$ are each independently selected from hydrogen or (1-4C)alkyl; and;

$Q_1$ is (1-6C)alkyl, (2-6C)alkenyl, (2-6C)alkynyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; and wherein $Q_1$ is optionally further substituted by one or more substituents independently selected from halogeno, hydroxyl, $NR^cR^d$, $[NR^cR^dR^e]^+$, (1-6C)alkyl, (1-6C)alkoxy, nitro, cyano, formyl, carboxy, carbamoyl, ureido, isocyano, sulphonyl, sulphonate, trifluoromethyl, mercapto.

(36) Ring B is phenyl optionally substituted, in either or both of the ortho- and/or para-position relative to the imine carbon atom to which ring B is attached, by one or more groups selected from halogeno, hydroxyl, $NR^cR^d$, (1-6C)alkyl, (1-6C)alkoxy, $[NR^cR^dR^e]^+$, nitro, cyano, formyl, carboxy, carbamoyl, sulphamoyl, ureido, isocyano, sulphonyl, sulphonate, trihalomethyl (e.g. trifluoromethyl), mercapto, wherein $R^c$, $R^d$, and $R^e$ are each independently selected from hydrogen or (1-6C)alkyl, or aryl (e.g. phenyl); or a group of the formula:

$L_1$-$Q_1$ wherein:
$L_1$ is absent or is selected from O, S, SO, $SO_2$, $N(R^f)$, C(O), $CH(OR^f)$, $C(O)N(R^f)$, $N(R^f)C(O)$, $N(R^f)C(O)N(R^g)$, $S(O)_2N(R^f)$, or $N(R^f)SO_2$, wherein $R^f$ and $R^g$ are each independently selected from hydrogen or (1-4C)alkyl; and;

$Q_1$ is (1-6C)alkyl, (2-6C)alkenyl, (2-6C)alkynyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; and wherein $Q_1$ is optionally further substituted by one or more substituents independently selected from halogeno, hydroxyl, $NR^cR^d$, $[NR^cR^dR^e]^+$, (1-6C)alkyl, (1-6C)alkoxy, nitro, cyano, formyl, carboxy, carbamoyl, ureido, isocyano, sulphonyl, sulphonate, trifluoromethyl, mercapto.

(37) Ring B is phenyl optionally substituted, in either or both of the ortho- and/or para-position relative to the imine carbon atom to which ring B is attached, by (1-3C) alkoxy.
(38) $R_1$ is (2-4C)alkylene linked to ring B to form a fused 5-, 6-, or 7-membered ring, optionally substituted as defined herein.
(39) $R_1$ is (3C)alkylene linked to ring B to form a fused 6-membered ring, optionally substituted as defined herein.
(40) $R_1$ is unsubstituted (3C)alkylene linked to ring B to form a fused 6-membered ring.

In a particular group of compounds of the invention, Ring B is phenyl optionally substituted as defined hereinbefore, i.e. the compounds have the structural formula A1 shown below:

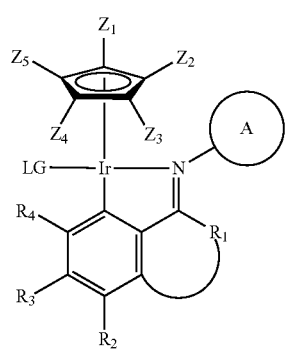

Formula A1 wherein ring A, $R_1$, $Z_1$, $Z_2$, $Z_3$, $Z_4$, $Z_5$, and LG are as defined herein, and $R_2$, $R_3$, and $R_4$ are each independently selected from hydrogen or any of the optional substituents for ring B defined herein.

In a particular group of compounds of the invention, Ring B is phenyl optionally substituted as shown, and Ring A is phenyl optionally substituted as shown, i.e. the compounds have the structural formula A2 shown below:

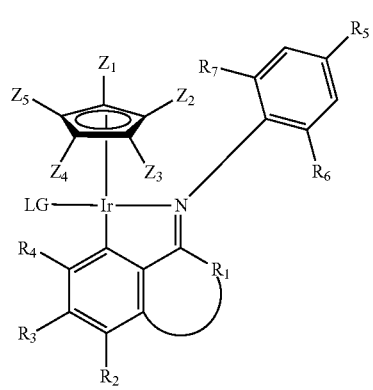

Formula A2 wherein $R_1$, $Z_1$, $Z_2$, $Z_3$, $Z_4$, $Z_5$, and LG are as defined herein, $R_2$, $R_3$, and $R_4$ are each independently selected from hydrogen or any of the optional substituents for ring B defined herein, and at least one of $R_5$, $R_6$, and $R_7$ are hydrogen, and the others of $R_8$, $R_9$, and $R_{10}$ are each independently selected from hydrogen or any of the optional substituents for ring A defined herein. In a particular embodiment, one or two of $R_5$, $R_6$, and $R_7$ are methoxy. In a particular embodiment, $R_5$ is methoxy and $R_6$ and $R_7$ are both hydrogen.

In a particular group of compounds of the invention, Ring B is phenyl optionally substituted as shown, and Ring A is phenyl optionally substituted as shown, i.e. the compounds have the structural formula A3 shown below:

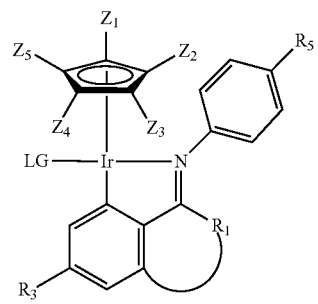

Formula A3 wherein $R_1$, $Z_1$, $Z_2$, $Z_3$, $Z_4$, $Z_5$, and LG are as defined herein, $R_3$ is selected from hydrogen or any of the optional substituents for ring B defined herein, $R_5$ is hydrogen or is selected from any of the optional substituents for ring A defined herein. In a particular embodiment, $R_5$ is methoxy and $R_3$ is either hydrogen or methoxy.

In a particular group of compounds of the invention, Ring B is phenyl optionally substituted as shown, Ring A is phenyl optionally substituted as shown, and $R_1$ is a propylene group linked to ring B to form a six-membered ring, i.e. the compounds have the structural formula A4 shown below:

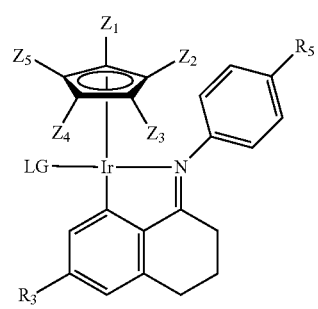

Formula A4 wherein $Z_1$, $Z_2$, $Z_3$, $Z_4$, $Z_5$, and LG are as defined herein, $R_3$ is selected from hydrogen or any of the optional substituents for ring B defined herein, $R_5$ is hydrogen or is selected from any of the optional substituents for ring A defined herein. In a particular embodiment, $R_5$ is methoxy, $R_3$ is either hydrogen or methoxy, and all of $Z_1$, $Z_2$, $Z_3$, $Z_4$, and $Z_5$ are methyl.

In a particular embodiment, the catalyst compound is selected from:

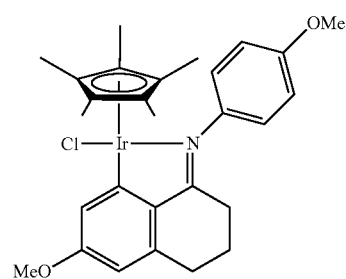

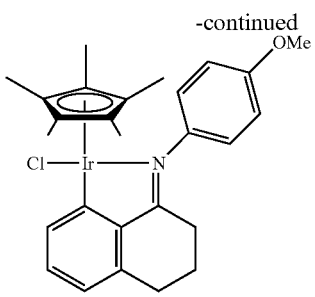

Preparation of the Catalyst Compounds of the Invention

In accordance with a second aspect of the present invention there is provided a method for preparing a catalyst compound of Formula I as defined herein, the method comprising:

reacting a compound of formula II:

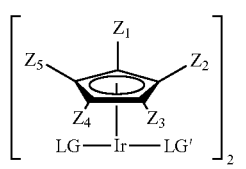

Formula II wherein $Z_1$, $Z_2$, $Z_3$, $Z_4$, $Z_5$, and LG are as defined herein, and LG' is a leaving group (optionally independently defined by any of the meanings given herein for LG);

with a compound of Formula III:

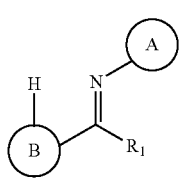

Formula III wherein ring A, ring B, and $R_1$ are as defined herein.

Though the compound of Formula II is shown as a dimer, it will be understood by those skilled in the art that this compound may also exist as a monomer, suitably solvated by virtue of a solvent molecule coordinating to the iridium atom. As such, the definition of the compound of Formula II is intended to include such equivalent monomeric forms.

According to a further aspect of the present invention, there is provided a catalyst compound of Formula I obtainable by, obtained by, or directly obtained by the method as defined herein for preparing a catalyst compound of Formula I.

Though LG' may have any one of the definitions given herein in relation to LG, LG' may be either the same as or different to LG.

In a particular embodiment, LG' is halogeno (e.g. chloro, bromo, iodo), carboxylate (e.g. acetate, trifluoroacetate), sulfonate (e.g. triflate, tosylate, mesylate), nitrate, phosphate, phenolate.

In a particular embodiment, LG' is halogeno (e.g. chloro, bromo, iodo), or carboxylate (e.g. acetate, trifluoroacetate).

In a particular embodiment, LG' is chloro.

In a particular embodiment, LG and LG' are both the same, most suitably both chloro.

Suitably the method involves reacting 1 molar equivalent of the compound of Formula II with between 1 and 10 molar equivalents of the compound of Formula III, more suitably between 1.2 and 5 molar equivalents of the compound of Formula III, most suitably between 1.5 and 2.5 molar equivalents of the compound of Formula III. Herein, the term molar equivalent is used to illustrate relative molar ratios of different substances, wherein the 1 molar equivalent used in relation to the compound of Formula II is a reference quantity in moles.

In an embodiment, the reaction is performed in the presence of a base, suitably between 1 and 20 molar equivalents of base, more suitably between 1.2 and 12 molar equivalents of base, most suitably 8 to 12 molar equivalents of base (i.e. relative to the 1 molar equivalent reference used in relation to the compound of Formula II). In an embodiment, the base is sodium acetate, though a host of other suitable bases would be apparent to those skilled in the art.

Suitably, the reaction is performed under a (substantially) inert atmosphere, e.g. under a nitrogen or argon atmosphere.

The reaction is suitably performed in a solvent, suitably an organic solvent. Though a range of organic solvents may be used, in a particular embodiment the organic solvent is dichloromethane.

The reaction is suitably allowed to proceed to completion, which typically takes at least 1 hour, more suitably at least 12 hours.

The reaction is suitably allowed to proceed at a temperature between 10 and 80° C.

The catalyst compound of Formula I is suitably isolated from the reaction mixture after the reaction is complete, typically by removing the reaction solvent to provide a solid, which is then subsequently washed with further organic solvents (e.g. hexane and/or diethyl ether). Optionally, before the reaction solvents are removed, the reaction mixture may be filtered (e.g. through celite) and optionally dried (e.g. over $MgSO_4$).

In accordance with a seventh aspect of the present invention there is provided a method for preparing a catalyst compound of Formula A as defined herein, the method comprising:

reacting a compound of formula II:

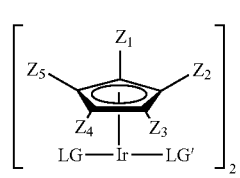

Formula II wherein $Z_1$, $Z_2$, $Z_3$, $Z_4$, $Z_5$, and LG are as defined herein, and LG' is a leaving group (optionally independently defined by any of the meanings given herein for LG);

with a compound of Formula B:

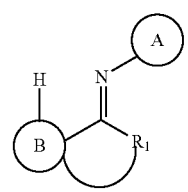

Formula B wherein ring A, ring B, and $R_1$ are as defined herein.

Again, though the compound of Formula II is shown as a dimer, it will be understood by those skilled in the art that this compound may also exist as a monomer, suitably solvated by virtue of a solvent molecule coordinating to the iridium atom. As such, the definition of the compound of Formula II is intended to include such equivalent monomeric forms.

According to a further aspect of the present invention, there is provided a catalyst compound of Formula A obtainable by, obtained by, or directly obtained by the method as defined herein for preparing a catalyst compound of Formula A.

LG' is suitably defined in the same manner as per the method of preparing the catalyst compound of Formula I.

Suitably the method involves reacting 1 molar equivalent of the compound of Formula II with between 1 and 10 molar equivalents of the compound of Formula B, more suitably between 1.2 and 5 molar equivalents of the compound of Formula B, most suitably between 1.5 and 2.5 molar equivalents of the compound of Formula B.

In an embodiment, the reaction is performed in the presence of a base, suitably between 1 and 20 molar equivalents of base, more suitably between 1.2 and 12 molar equivalents of base, most suitably 8 to 12 molar equivalents of base (i.e. relative to the 1 molar equivalent reference used in relation to the compound of Formula II). In an embodiment, the base is sodium acetate, though a host of other suitable bases would be apparent to those skilled in the art.

Suitably, the reaction is performed under a (substantially) inert atmosphere, e.g. under a nitrogen or argon atmosphere.

The reaction is suitably performed in a solvent, suitably an organic solvent. Though a range of organic solvents may be used, in a particular embodiment the organic solvent is dichloromethane.

The reaction is suitably allowed to proceed to completion, which typically takes at least 1 hour, more suitably at least 12 hours.

The reaction is suitably allowed to proceed at a temperature between 10 and 80° C.

The catalyst compound of Formula I is suitably isolated from the reaction mixture after the reaction is complete, typically by removing the reaction solvent to provide a solid, which is then subsequently washed with further organic solvents (e.g. hexane and/or diethyl ether). Optionally, before the reaction solvents are removed, the reaction mixture may be filtered (e.g. through celite) and optionally dried (e.g. over $MgSO_4$).

Method of Reducing a Reducible Substrate

In accordance with a third aspect of the present invention there is provided a method of reducing a reducible substrate, the method comprising hydrogenating the reducible substrate in the presence of a catalyst compound of Formula I as defined herein.

In accordance with an eighth aspect of the present invention there is provided a method of reducing a reducible substrate, the method comprising hydrogenating the reducible substrate in the presence of a catalyst compound of Formula A as defined herein.

According to a further aspect of the present invention there is provided a hydrogenated substrate obtainable by, obtained by, or directly obtained by any one of the methods as defined herein for reducing a reducible substrate.

In the description of the synthetic methods described below and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

The methodologies of the present invention, which are discussed below in more detail, generally involve the hydrogenation of a reducible substrate in an appropriate solvent in the presence of a sufficient loading of the catalyst. Other conditions such as temperature, pH, reaction times, additional reagents, and reaction mixture agitation are also discussed below.

Unless otherwise stated, the following features apply equally to both catalyst compounds of Formula I and Formula A regarding their use in methods of reducing a reducible substrate.

Reducible Substrate

The reducible substrate comprises at least one reducible moiety which is reducible by the method(s) of the present invention. In an embodiment, the reducible substrate comprises a single reducible moiety. In other embodiments, the reducible substrate comprises a plurality of reducible moieties, which may either all be reduced or some selectively reduced by the method(s) of the invention.

It will be apparent to those skilled in the art that the methodology according to the invention is broadly applicable to a diverse range of reducible substrates. Moreover, in the light of this disclosure the skilled artisan can readily appreciate that the methodology of the invention is especially applicable to reducing reducible moieties such as those comprising polar π-bonds. As such, the reducible substrate (or a reducible moiety thereof) suitably comprises a polar π-bond (e.g. a C=Q moiety, where Q is a group more electronegative than the carbon atom to which it is attached).

In a particular embodiment, the reducible substrate comprises a reducible moiety selected from the group including an imine, iminium, carbonyl, oxonium, thiocarbonyl, thioxonium, or an alkene or alkyne in π-conjugation with a nitro, cyano, formyl, carboxy, carbamoyl, sulphamoyl, ureido, isocyano, sulphonyl, or sulphonate group. In a particular embodiment, the reducible substrate comprises a reducible moiety selected from an imine and an iminium group (optionally made in situ—i.e. as per a reductive amination procedure). The reducible moiety is reduced by the method of the present invention.

In a particular embodiment, the reducible substrate is defined by a compound of Formula X:

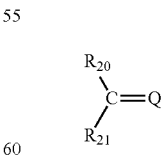

Formula X wherein $R_{20}$ and $R_{21}$ are each independently selected from hydrogen, (1-8C)alkyl, (2-8C)alkenyl, (2-8C)alkynyl, (3-8C)cycloalkyl, (3-8C)cycloalkyl-(1-6C)alkyl, (3-8C)cycloalkenyl, (3-8C)cycloalkenyl-(1-6C)alkyl, (3-8C)cycloalkynyl, (3-8C)cycloalkynyl-(1-6C)alkyl, heterocyclyl, heterocyclyl-(1-6C)alkyl, aryl, aryl-(1-

6C)alkyl, heteroaryl, heteroaryl-(1-6C)alkyl; and wherein $R_{20}$ and $R_{21}$ are optionally substituted by one or more substituent groups selected from halogeno, hydroxyl, $NR^rR^s$, (1-6C)alkyl, (1-6C)alkoxy, $[NR^rR^sR^t]^+$, nitro, cyano, formyl, carboxy, carbamoyl, sulphamoyl, ureido, isocyano, sulphonyl, sulphonate, trihalomethyl (e.g. trifluoromethyl), mercapto, wherein $R^r$, $R^s$, and $R^t$ are each independently selected from hydrogen or (1-6C)alkyl, or aryl (e.g. phenyl); or a substituent group of the formula:

$L_3$-$Q_3$ wherein:
  $L_3$ is absent or is selected from O, S, SO, $SO_2$, $N(R^u)$, C(O), $CH(OR^u)$, $C(O)N(R^u)$, $N(R^u)C(O)$, $N(R^u)C(O)N(R^v)$, $S(O)_2N(R^u)$, or $N(R^u)SO_2$, wherein $R^u$ and $R^v$ are each independently selected from hydrogen or (1-4C)alkyl; and;
  $Q_3$ is (1-6C)alkyl, (2-6C)alkenyl, (2-6C)alkynyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; and wherein $Q_3$ is optionally further substituted by one or more substituents independently selected from halogeno, hydroxyl, $NR^rR^s$, $[NR^rR^sR^t]^+$, (1-6C)alkyl, (1-6C)alkoxy, nitro, cyano, formyl, carboxy, carbamoyl, ureido, isocyano, sulphonyl, sulphonate, trifluoromethyl, mercapto;
  wherein any two substituent groups of either or both of $R_{20}$ and $R_{21}$ are optionally linked so as to form a 5-, 6-, or 7-membered ring;

Q is selected from O, $[OR_{23}]^+$, S, $[SR_{23}]^+$, $NR_{22}$, $[NR_{23}R_{24}]^+$ (where positively charged groups are associated with a suitable counterion), wherein:
  $R_{22}$, $R_{23}$ and $R_{24}$ are each independently selected from hydrogen, (1-8C)alkyl, (2-8C)alkenyl, (2-8C)alkynyl, (3-8C)cycloalkyl, (3-8C)cycloalkyl-(1-6C)alkyl, (3-8C)cycloalkenyl, (3-8C)cycloalkenyl-(1-6C)alkyl, (3-8C)cycloalkynyl, (3-8C)cycloalkynyl-(1-6C)alkyl, heterocyclyl, heterocyclyl-(1-6C)alkyl, aryl, aryl-(1-6C)alkyl, heteroaryl, heteroaryl-(1-6C)alkyl; and wherein $R_{22}$, $R_{23}$, and $R_{24}$ are each independently optionally further substituted by one or more substituent groups selected from halogeno, hydroxyl, $NR^wR^x$, (1-6C)alkyl, (1-6C)alkoxy, $[NR^wR^xR^y]^+$, nitro, cyano, formyl, carboxy, carbamoyl, sulphamoyl, ureido, isocyano, sulphonyl, sulphonate, trihalomethyl (e.g. trifluoromethyl), mercapto, wherein $R^w$, $R^x$, and $R^y$ are each independently selected from hydrogen or (1-6C)alkyl, or aryl (e.g. phenyl); or a substituent group of the formula:

$L_4$-$Q_4$ wherein:
  $L_4$ is absent or is selected from O, S, SO, $SO_2$, $N(R^{z1})$, C(O), $CH(OR^{z1})$, $C(O)N(R^{z1})$, $N(R^{z1})C(O)$, $N(R^{z1})C(O)N(R^{z2})$, $S(O)_2N(R^{z1})$, or $N(R^{z1})SO_2$, wherein $R^{z1}$ and $R^{z2}$ are each independently selected from hydrogen or (1-4C)alkyl; and;
  $Q_4$ is (1-6C)alkyl, (2-6C)alkenyl, (2-6C)alkynyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; and wherein $Q_4$ is optionally further substituted by one or more substituents independently selected from halogeno, hydroxyl, $NR^wR^x$, $[NR^wR^xR^y]^+$, (1-6C)alkyl, (1-6C)alkoxy, nitro, cyano, formyl, carboxy, carbamoyl, ureido, isocyano, sulphonyl, sulphonate, trifluoromethyl, mercapto;
  wherein any two substituent groups of $R_{22}$, $R_{23}$ and $R_{24}$ are optionally linked so as to form a 5-, 6-, or 7-membered ring;
  on the proviso that neither $R_{23}$ or $R_{24}$ are hydrogen;

or an acceptable salt thereof.

In a particular embodiment, $R_{20}$ and $R_{21}$ are each independently selected from (1-8C)alkyl, aryl, aryl-(1-6C)alkyl, heteroaryl, heteroaryl-(1-6C)alkyl; and wherein $R_{20}$ and $R_{21}$ are optionally substituted by one or more substituent groups selected from (1-6C)alkoxy, nitro, trihalomethyl (e.g. trifluoromethyl), or a substituent group of the formula:

$L_3$-$Q_3$ wherein:
  $L_3$ is absent; and
  $Q_3$ is aryl wherein any two substituent groups of either or both of $R_{20}$ and $R_{21}$ are optionally linked so as to form a 5-, 6-, or 7-membered ring.

In a particular embodiment, one of $R_{20}$ and $R_{21}$ is (1-3C)alkyl, whilst the other of $R_{20}$ and $R_{21}$ is aryl (e.g. phenyl, naphthyl, anthracenyl); and wherein said aryl group is optionally substituted by one or more substituent groups selected from (1-3C)alkoxy, nitro, trifluoromethyl, or phenyl; wherein any two substituent groups of either or both of $R_{20}$ and $R_{21}$ are optionally linked so as to form a 5-membered ring.

In a particular embodiment, Q is $NR_{22}$, or $[NR_{23}R_{24}]^+$ as defined herein, i.e. the reducible substrate is defined by a compound of Formula X1 or X2:

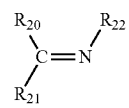

Formula X1

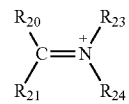

Formula X2 wherein $R_{20}$, $R_{21}$, $R_{22}$, $R_{23}$ and $R_{24}$ each have any of the meanings as defined herein.

In a particular embodiment, Q is $NR_{22}$ and $R_{22}$ is hydrogen. Ammonia or ammonium salts (e.g. ammonium formate) may suitably provide a source of ammonia to produce an imine with such a Q group.

Where the method is applied to a reducible substrate of Formula X, the reducible substrate (X) is reduced to a reduced product of Formula $XH_2$ according to the scheme below:

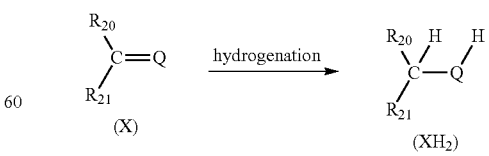

wherein $R_{20}$, $R_{21}$, and Q are as defined herein.

In a particular embodiment, the reducible substrate (i.e. the substrate being reduced in the method) may be pre-formed (i.e. prior to its reduction in accordance with the method). In an alternative embodiment, the reducible substrate is formed in situ (e.g. as per reductive aminations).

In a particular embodiment, the method of reducing is a method of reductive amination whereby the reducible substrate is an imine (e.g. Formula X1) or iminium (e.g. Formula X2) prepared in situ by a reaction between a ketone (e.g. of Formula X3) and ammonia or an amine (e.g. of either Formula X1' or Formula X2' or a salt thereof) as illustrated, by way of example, by the scheme below:

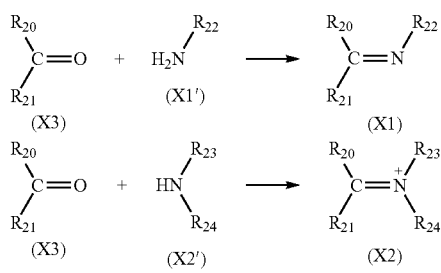

wherein $R_{20}$, $R_{21}$, $R_{22}$, $R_{23}$ and $R_{24}$ each have any of the meanings as defined herein.

In a particular embodiment, the amine is ammonia (optionally supplied by ammonium salts such as ammonium formate). In an embodiment, the ketone is a methyl-aryl-ketone.

During reductive aminations, hydrogenation conditions suitably prevail as the ketone reacts with the amine to form the imine or iminium. However, suitably under the prevailing conditions, the imine or iminium is more susceptible to hydrogenation than the corresponding ketone. As such, the imine or iminium is preferentially reduced.

Formulas given in relation to amines or imines may also include acceptable salts thereof. For instance, an imine may become protonated (e.g. at acid pHs) to yield an iminium ion. Alternatively, the amine starting materials (including ammonia) may themselves be provided as protonated salts (e.g. ammonium formate) where said salts still provide a source of the free amine under the relevant reaction conditions. Any cations are suitably associated with appropriate counterions (e.g. counterions usually depend on the prevailing conditions).

Hydrogenation

Hydrogenating the reducible substrate may suitably involve exposing the reducible substrate (and the catalyst compound) to a source of hydrogen.

In a particular embodiment, hydrogenating involves exposing the reducible substrate and catalyst compound to a gaseous hydrogen atmosphere, suitably a pressurized hydrogen atmosphere (e.g. 1-2000 Bar pressure, most suitably 1-100 Bar pressure). Suitably the reducible substrate and catalyst compound are agitated (e.g. stirred or shaken in a reaction solvent) during hydrogenation under a hydrogen atmosphere.

In an embodiment, hydrogenating the reducible substrate occurs via transfer hydrogenation. This involves providing an alternative source of hydrogen to gaseous hydrogen, i.e. from a "hydrogen donor". The skilled person can readily appreciate the benefits of transfer hydrogenation over standard hydrogenation, not least the added convenience and safety.

Transfer hydrogenation reactions may be carried out with a range of "hydrogen donors" known in the art (e.g. diimide, formic acid, formate, isopropanol, etc.). In a particular embodiment, the hydrogen donor comprises formic acid or formate. In a particular embodiment, the hydrogen donor comprises (or consists of) formic acid, ammonium formate, a metal formate (e.g. sodium formate), or a mixture thereof. In a particular embodiment, the hydrogen donor comprises (or consists of) ammonium formate.

It is well understood that during transfer hydrogenation reactions, one molar equivalent of formic acid or formate breaks down in the presence of a suitable catalyst to form 1 molar equivalent of hydrogen along with 1 molar equivalent of carbon dioxide. The hydrogen, which generally exists as metal hydride, is then available to participate in the transfer hydrogenation reaction.

The transfer hydrogenation reaction mixture suitably comprises a hydrogen donor in an amount sufficient to provide at least 1 molar equivalent of hydrogen per molar equivalent of reducible moiety of the reducible substrate, more suitably at least 2 molar equivalents of hydrogen per molar equivalent of reducible moiety, most suitably at least 5 molar equivalents of hydrogen per molar equivalent of reducible moiety. The transfer hydrogen reaction mixture may suitably comprise a hydrogen donor in an amount sufficient to provide at most 50 molar equivalents of hydrogen per molar equivalent of reducible moiety, more suitably at most 20 molar equivalents of hydrogen per molar equivalent of reducible moiety, most suitably at most 15 molar equivalents of hydrogen per molar equivalent of reducible moiety.

Where transfer hydrogenation is employed, the hydrogenation reaction suitably takes place under an otherwise inert atmosphere (e.g. of nitrogen or argon).

Solvent

The method(s) of reducing according to the invention are suitably performed in an appropriate hydrogenation solvent, which may be chosen from a variety of solvents, for example, to suit the particular conditions, reagents, substrate, and/or product.

A particular solvent or solvent combination may be selected for a variety of reasons, including inter alia reagent solubilities (including of the reducible substrate and catalyst), solvent boiling point (whether to achieve higher temperatures if required to effect hydrogenation or to facilitate facile post-reaction removal of a low-boiling solvent), ease of crystallisation of the product therefrom (with or without a co-solvent), safety considerations, solvent availability, and cost. However, the solvent may also be selected to suit the catalyst, for instance to facilitate dissociation of the catalyst leaving group to enhance catalytic activity, or to inhibit coordination of the substrate and product to the metal centre.

In a particular embodiment the hydrogenation solvent comprises a polar protic or aprotic solvent. Suitably a solvent is considered "polar" where it is miscible with water. In a particular embodiment, the hydrogenation solvent comprises a polar protic solvent. In another embodiment, the solvent comprises a (1-3C)alcohol, optionally substituted by one or more halides (e.g. fluoro, an example of which is trifluoroethanol (TFE)).

In a particular embodiment, where the catalyst used is the catalyst compound of Formula I, the hydrogenation solvent comprises a (1-3C)alcohol, suitably a (1-2C)alcohol, most suitably methanol.

In a particular embodiment, where the catalyst used is the catalyst compound of Formula A, the hydrogenation solvent comprises a (2-3C)alcohol optionally substituted by one or more halides, most suitably trifluoroethanol (TFE).

The hydrogenation solvent may comprise a mixture of two or more solvents. However, in a particular embodiment, the hydrogenation solvent comprises at least 80% w/w (relative to the total amount of hydrogenation solvent) of any one of the single solvents referred to above in relation to the hydrogenation solvent, more suitably at least 90%. In a particular embodiment, the hydrogenation solvent is any one of the single solvents referred to above in relation to the hydrogen solvent.

Suitably the catalyst is pre-dissolved in a portion of the hydrogenation solvent before its addition to the hydrogenation reaction mixture.

The skilled person will appreciate that the particular catalyst compounds of the present invention may provide particular advantages over those of the prior art in particular solvents.

Acid

In particular embodiments, especially in respect of reductive aminations, the hydrogenation reaction mixture comprises an acid or acidic buffer, suitably comprising an organic acid. Suitably, sufficient acid or acidic buffer is used to provide a starting pH (i.e. the pH before hydrogenation is initiated) between pH 3-8. Suitably the acid or acidic buffer is not itself susceptive to hydrogenation or reaction with the catalyst. However, the acid or acidic buffer may provide an additional source of hydrogen, e.g. if formic acid is used.

In a particular embodiment, the acid (or acid associated with the acid buffer) has a $pK_a$ in water (at 25° C.) of greater than or equal to 3, suitably greater than or equal to 3.5.

In particular embodiments, the acid or acid buffer is selected from the group including formic acid, acetic acid, benzoic acid, phosphoric acid, citric acid, phthalic acid, and formic acid/triethylamine azeotrope.

Catalyst Loading

The hydrogenation reaction mixture suitably comprises sufficient catalyst compound for effective hydrogenation of the reducible substrate. Suitably the reaction mixture comprises at least 0.000001 molar equivalents of the catalyst compound per molar equivalent of reducible moiety of the reducible substrate, more suitably at least 0.0001 molar equivalents of the catalyst compound per molar equivalent of reducible moiety of the reducible substrate, most suitably at least 0.0003 molar equivalents of the catalyst compound per molar equivalent of reducible moiety of the reducible substrate. Suitably the reaction mixture comprises at most 0.1 molar equivalents of the catalyst compound per molar equivalent of reducible moiety of the reducible substrate, more suitably at most 0.01 molar equivalents of the catalyst compound per molar equivalent of reducible moiety of the reducible substrate, most suitably at most 0.005 molar equivalents of the catalyst compound per molar equivalent of reducible moiety of the reducible substrate.

Other Reaction Conditions

Suitably, the reduction reaction may be carried out under anhydrous conditions.

For standard hydrogenation conditions, the reaction is suitably carried out under an atmosphere of hydrogen, optionally under greater pressure than atmospheric pressure. Transfer hydrogenation reactions, on the other hand, may be suitably carried out in the presence of an inert atmosphere, such as argon or nitrogen.

Hydrogenation reactions of the invention are suitably carried out at elevated temperature (e.g. above room temperature, i.e. above 25° C.). Suitably hydrogenation reactions are carried out at greater than or equal to 40° C., more suitably at greater than or equal to 60° C., most suitably at greater than or equal to 75° C. Suitably hydrogenation reactions are carried out at less than or equal to 120° C., more suitably at less than or equal to 100° C., most suitably at less than or equal to 90° C.

When using standard hydrogenation conditions (i.e. with gaseous hydrogen), the hydrogenation reactions suitably proceed under at least 2 Bar of pressure, more suitably at least 4 Bar, most suitably at least 15 Bar. When using standard hydrogenation conditions, the hydrogenation reactions suitably proceed under at most 2000 Bar of pressure, more suitably at most 100 Bar, most suitably at most 30 Bar.

When using transfer hydrogenation conditions, the hydrogenation reactions suitably proceed under atmospheric pressure (e.g. about 1 Bar pressure).

The duration of hydrogenation reactions is suitably at least 10 minutes, suitably at least 30 minutes, suitably at least 5 hours. The duration of hydrogenation reactions is suitably at most 48 hours, suitably at most 24 hours, suitably at most 12 hours, suitably at most 7 hours.

A person skilled in the art will be able to select appropriate reaction conditions to use in order to facilitate this reaction. Moreover, the resulting hydrogenated substrate can be isolated and purified using techniques well known in the art.

The reaction conditions suitably provide for at least 30% completion of the hydrogenation reaction (as measured via in-process checks, e.g. liquid chromatography, or via isolated yields), suitably at least 50% completion, more suitably at least 70% completion, most suitably at least 90% completion. It will be understood that where hydrogenation reactions do not proceed to completion, hydrogenated substrate (i.e. the product) may still be recovered and separated from other reagents, intermediates and starting materials by techniques well known in the art, including via workups, crystallisation, and chromatography.

Compositions

In accordance with a fourth aspect of the present invention there is provided a composition comprising the catalyst compound of Formula I as defined herein.

In accordance with a ninth aspect of the present invention there is provided a composition comprising the catalyst compound of Formula A as defined herein.

Such catalyst compositions may comprise an additional catalyst, suitably an additional hydrogenation catalyst such as the well-known Wilkinson's rhodium and ruthenium catalysts and the Crabtree's iridium catalyst.

The catalyst composition may comprise a solvent, suitably a solvent which dissolves the catalyst compound, suitably a solvent compatible with the hydrogenation reactions for which the catalyst compound is intended.

The catalyst composition may optionally comprise the catalyst compound upon a solid support.

The catalyst composition may optionally comprise the catalyst compound dispersed within a solid carrier (e.g. carbon).

Kit of Parts

In accordance with a fifth aspect of the present invention there is provided a kit of parts comprising the compound of Formula II as defined herein and the compound of Formula III as defined herein.

In accordance with a tenth aspect of the present invention there is provided a kit of parts comprising the compound of Formula II as defined herein and the compound of Formula B as defined herein.

Such kits are ideal where it is desirable to form the catalyst on site or in situ, rather than, for example obtaining the pre-formed catalyst from a commercial source. In certain embodiments, it is desirable to form a "fresh" batch of the catalyst prior to its use in hydrogenation reactions of the present invention.

EXAMPLES

Catalyst Compound of Formula I

Materials and Equipment

Unless otherwise specified, all reagents were commercially purchased from Aldrich, Alfa Aesar, Acros organics, Apollo scientific, or Fluorochem and used without further purification. Molecular sieves (4 Å) were heated in oven at 160° C. overnight prior to use. NMR spectra were recorded on a Brucker 400 MHz NMR spectrometer with TMS as an internal standard, all at ambient temperature.

Example 1

General Procedures for the Synthesis of Imines (i.e. Those Used for Producing the Catalyst)

Amine (20 mmol), ketone (20 mmol), NaHCO$_3$ (2.52 g, 30 mmol), molecular sieves (8 g, 4 Å) were dissolved in toluene (50 ml) in a Schlenk tube. The reaction mixture was exposed to nitrogen atmosphere and heated to reflux for 24 hrs. The reaction mixture was cooled and filtered through celite. The celite washed with DCM, filtrate was collected and the solvents were evaporated in vacuo. The resultant solid was washed with diethyl ether and recrystallised using hexane/DCM.

Example 2

General Procedure for the Preparation of Cyclometalated Complexes

[Cp*IrCl$_2$]$_2$ (1 equiv.), imine ligand (2.2 equiv.) and NaOAc (10 equiv.) were placed into a Schlenk tube. The tube was degassed and charged with nitrogen prior to the addition of DCM (5 ml). The resulting mixture was stirred for 24 hr at 27° C. The reaction mixture was filtered through celite and dried over magnesium sulphate. The solvent was removed under vacuum and the resultant solid was washed with hexane and diethyl ether.

Specific examples are now described.

Comparative Example 2a

Preparation of (E)-4-(1-((4-methoxyphenyl)imino) ethyl)benzonitrile iridium complex 2a (p-methoxyphenyl/p-cyanophenyl derivative)

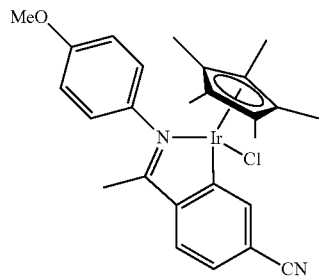

2a

The product, already disclosed in the prior art, was obtained as a deep red solid the general procedure for the preparation of cyclometalated complexes in 17 h; $^1$H NMR (400 MHz, 253 K, CDCl$_3$) δ 1.44 (s, 15H), 2.47 (s, 3H), 3.88 (s, 3H), 6.82-6.83 (m, 1H), 6.93 (d, J=5.8 Hz, 1H), 7.02 (d, J=5.9 Hz, 1H), 7.33 (d, J=7.6 Hz, 1H), 7.56 (d, J=7.6 Hz, 1H), 7.77 (d, J=7.8 Hz, 1H), 8.05 (s, 1H) ppm; $^{13}$C NMR (100 MHz, 253 K, CDCl$_3$) δ 8.8, 17.5, 55.7, 90.0, 112.5, 114.3, 115.1, 120.1, 123.1, 125.2, 128.2, 138.2, 138.3, 143.6, 151.8, 157.9, 167.4, 180.9 ppm; Anal Calcd for C$_{26}$H$_{28}$ClIrN$_2$O: C, 51.01; H, 4.61; N, 4.58. Found: C, 51.02; H, 4.65; N, 4.42.

Comparative Example 2b

Preparation of (E)-4-methoxy-N-(1-(4-methoxyphenyl)ethylidene)aniline iridium complex 2b (p-methoxyphenyl/p-methoxyphenyl derivative)

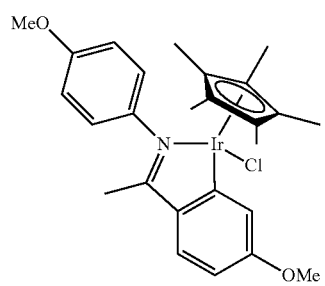

2b

The product, already disclosed in the prior art, was obtained as a bright yellow solid the general procedure for the preparation of cyclometalated complexes in 17 h; $^1$H NMR (400 MHz, 253 K, CDCl$_3$) δ 1.44 (s, 15H), 2.41 (s, 3H), 3.87 (s, 3H), 3.93 (s, 3H), 6.61 (dd, J=8.5, 2.4 Hz, 1H), 6.81 (d, J=8.4 Hz, 1H), 6.90 (d, J=8.4 Hz, 1H), 6.98 (d, J=8.4 Hz, 1H), 7.35 (d, J=2.4 Hz, 1H), 7.49 (d, J=8.5 Hz, 1H), 7.80 (d, J=8.4 Hz, 1H) ppm; $^{13}$C NMR (100 MHz, 253 K, CDCl$_3$) δ 8.8, 17.1, 55.2, 55.6, 89.0, 107.6, 112.2, 114.8, 119.1, 123.8, 125.2, 130.2, 141.2, 144.2, 157.3, 161.9, 170.3, 180.1 ppm; Anal Calcd for C$_{26}$H$_{31}$ClIrNO$_2$: C, 50.60; H, 5.06; N, 2.27. Found: C, 50.60; H, 4.93; N, 2.16.

Example 2c

Preparation of (E)-4-methoxy-N-(1-(naphthalen-2-yl)ethylidene)aniline iridium complex 2c (p-methoxyphenyl/p-β,β-naphthyl derivative)

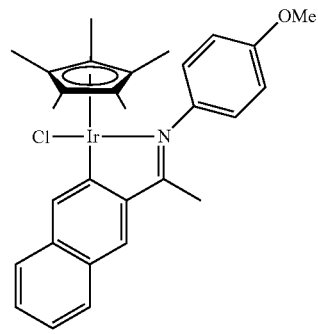

2c

The product was obtained as an orange solid according to the general procedure for the preparation of cyclometalated complexes; $^1$H NMR (CD$_2$Cl$_2$, 400 MHz, 293 K) δ 8.10 (s, 1H), 8.04 (s, 1H), 7.80 (dd, J=8.2 Hz, 4.4 Hz, 0.5 Hz, 2H), 7.46 (ddd, J=8.2 Hz, 6.9 Hz, 1.3 Hz, 1H), 7.32 (ddd, J=8.1 Hz, 6.9 Hz, 1.2 Hz, 1H), 7.02-6.91 (m, 4H), 3.86 (s, 3H), 2.53 (s, 3H), 1.44 (s, 15H) ppm; $^{13}$C NMR (CD$_2$Cl$_2$, 100 MHz, 273

K) δ 181.9, 160.7, 158.8, 149.4, 145.0, 137.5, 132.9, 130.3, 129.8, 129.3, 128.1, 126.8, 125.0, 124.2, 89.8, 56.3, 17.6, 9.1 ppm; Anal. calc. for $C_{29}H_{31}ClIrNO$ (%): C, 54.66; H, 4.90; N, 2.20. Found: C, 54.33; H, 4.90; N, 2.06. HRMS-FAB for $C_{29}H_{31}Cl^{191}IrNO$ calc: 635.1695. found: 635.1692.

Example 2d

Preparation of (E)-4-methoxy-N-(1-(6-methoxynaphthalen-2-yl)ethylidene)aniline iridium complex 2d (p-methoxyphenyl/p-methoxy-β,β-naphthyl derivative)

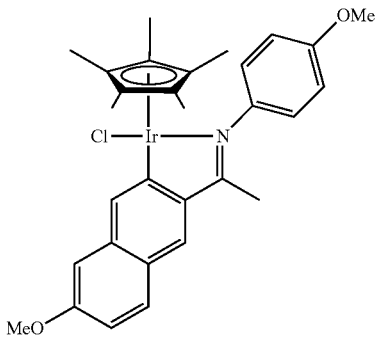

The product was obtained as an orange solid according to the general procedure for the preparation of cyclometalated complexes; $^1$H NMR (CDCl$_3$, 400 MHz, 273 K) δ (ppm): 8.02 (s, 1H), 7.92 (s, 1H), 7.86 (s, 1H), 7.65 (d, J=8.9 Hz, 1H), 7.19-6.80 ppm (m, 5H), 3.95 (s, 3H), 3.86 (s, 3H), 2.51 (s, 3H), 1.47 (s, 15H). $^{13}$C NMR (CD$_2$Cl$_2$, 100 MHz, 273 K) δ (ppm): 181.5, 161.3, 159.4, 158.2, 154.7, 146.7, 144.7, 138.9, 136.0, 131.6, 131.1, 129.2, 125.5, 116.8, 104.7, 89.3, 56.0, 55.7, 17.3, 9.04. HRMS: [M–Cl]$^+$ calc: 632.2141. found; 632.2136.

Example 2e

Preparation of (E)-N-(1-(anthracen-2-yl)ethylidene)-4-methoxyaniline iridium complex 2e (p-methoxyphenyl/anthracene derivative)

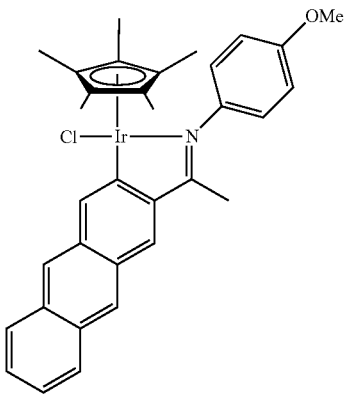

The product was obtained according to the general procedure for the preparation of cyclometalated complexes; High-resolution mass spectrometry gave [M+H]$^+$; calc: 652.2191. found: 652.2188.

Example 2f

Preparation of (E)-4-methoxy-N-(1-(phenanthren-2-yl)ethylidene)aniline iridium complex 2f (p-methoxyphenyl/phenanthrene derivative)

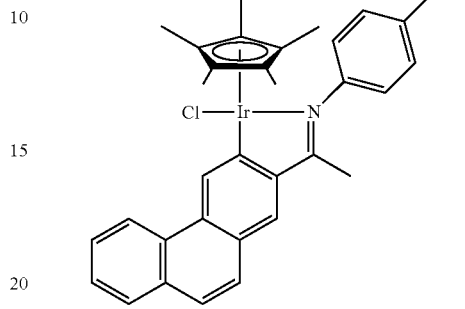

The product was obtained as a red solid according to the general procedure for the preparation of cyclometalated complexes; $^1$H NMR (CD$_2$Cl$_2$, 400 MHz, 273 K) δ (ppm): 9.04 (s, 1H), 8.85 (d, J=8.18, 1H), 8.05 (s, 1H), 7.87 (dd, J=7.8 Hz, 1.3 Hz, 1H), 7.72 (d, J=8.7, 1H), 7.67 (ddd, J=8.2, 7.0 Hz, 1.4 Hz, 1H), 7.63-7.58 (m, 2H), 7.06-6.94 (m, 4H), 3.86 (s, 3H), 2.58 (s, 3H), 1.50 (s, 15H); $^{13}$C NMR (CD$_2$Cl$_2$, 100 MHz, 273 K) δ (ppm): 181.9, 164.2, 158.8, 149.2, 145.0, 134.1, 133.8, 130.1, 129.3, 129.1, 128.6, 128.5, 128.1, 127.7, 126.9, 125.1, 124.9, 124.2, 90.1, 56.3, 17.6, 9.3; Anal. calc. for $C_{33}H_{33}ClIrNO$ (%): C, 57.67; H, 4.84; N, 2.04. Found: C, 57.58; H, 4.80; N, 1.91. HRMS: [M–Cl]$^+$; calc: 652.2191. found; 652.2188.

Example 3

General Procedure for the Transfer Hydrogenative Reductive Amination Using Ammonium Formate Ketone (0.5 mmol) and HCOONH$_4$ (5 mmol) were dissolved in MeOH (2 ml) in a carousel reaction tube. The mixture was than degassed and stirred for 10 minutes at 80° C. under nitrogen. HCOOH/NEt$_3$ azeotrope (0.5 ml) and catalyst solution (1 ml) (prepared by dissolving catalyst (0.5 μmol) in MeOH (1 ml)) were then introduced. The resulting mixture was stirred at 80° C. for the time indicated. The reaction was quenched with water, basified with aqueous KOH solution and extracted with DCM. The solvent was then removed under vacuum. The crude product was dissolved in ethanol (10 ml) and 6 N HCl solution (5 ml) was than added. The mixture was refluxed for 6 hrs. Ethanol was then removed under vacuum and the resultant aqueous layer was washed with ethyl acetate to remove impurities. The aqueous layer was basified with a KOH solution and extracted with DCM. The organic layers were combined and dried over sodium sulphate. The final product was obtained after the evaporation of solvent under vacuum.

The following experiments have been performed, by way of example, to illustrate the applicability of the present invention.

Catalyst Screen in Methanol

This general reaction procedure was then applied to the following reaction scheme, the results of the catalyst screen in methanol are presented in Table 1 below.

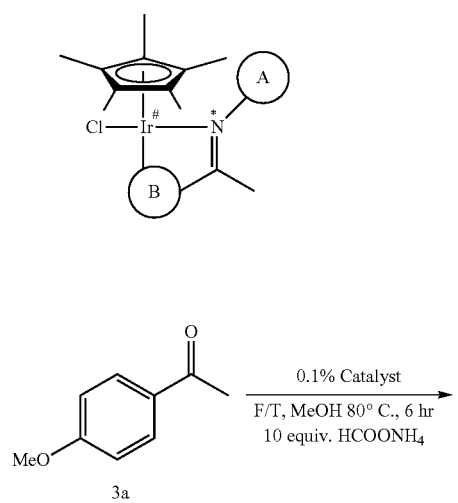

TABLE 1

| Catalyst screening in MeOH | |
|---|---|
| Catalyst | Conversion (%)[b] |
| [Cp*IrCl₂]₂ | N/R |
| A = p-OMe—Ph, B = p-CN—Ph, 2a | 2 |
| A = p-OMe—Ph, B = p-OMe—Ph, 2b | 22 |
| A = p-OMe—Ph, B = (2c, naphthalene) | 96 |
| A = p-OMe—Ph, B = (2d, MeO-naphthalene) | 52 |
| A = p-OMe—Ph, B = (2e, anthracene) | 72 |
| A = p-OMe—Ph, B = (2f, phenanthrene) | 4 |

[a] General condition: Ketone (0.5 mmol), Catalyst (5 × 10⁻⁴ mmol), F/T (0.5 ml), HCO₂NH₄ (5 mmol), MeOH (3.0 ml), 6 hr, 80° C.
[b] Determined by ¹H-NMR.

FIG. 1 is a graph showing a comparison of the catalytic activity of catalyst compounds 2b (prior art compound—solid squares) and 2c (compound of the invention—solid diamonds) in the illustrated reductive amination in MeOH.

Catalyst Screen in Trifluoroethanol (TFE)

This general reaction procedure was then applied to the following reaction scheme, the results of the catalyst screen in trifluoroethanol (TFE) are presented in Table 2 below.

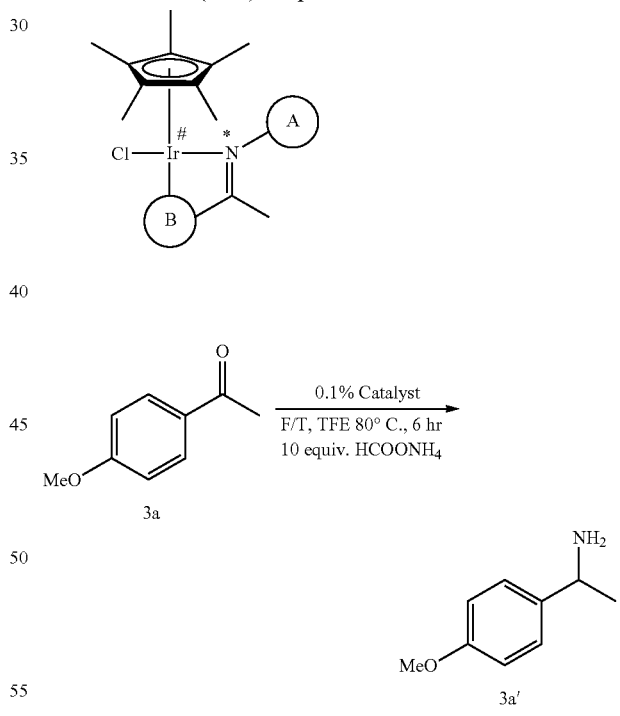

TABLE 2

| Catalyst screening in TFE | |
|---|---|
| Catalyst | Conversion (%)[b] |
| [Cp*IrCl₂]₂ | N/R |
| A = p-OMe—Ph, B = p-CN—Ph, 2a | 36 |
| A = p-OMe—Ph, B = p-OMe—Ph, 2b | 28 |

TABLE 2-continued

Catalyst screening in TFE

| Catalyst | Conversion (%)[b] |
|---|---|
| A = p-OMe—Ph, B = (2c) | 8 |
| A = p-OMe—Ph, B = (2d) | 72 |
| A = p-OMe—Ph, B = (2e) | 12 |
| A = p-OMe—Ph, B = (2f) | 13 |

[a]General condition: Ketone (0.5 mmol), Catalyst (5 × 10⁻⁴ mmol), F/T (0.5 ml), HCO₂NH₄ (5 mmol), MeOH (3.0 ml), 6 hr, 80° C.
[b]Determined by ¹H-NMR.

Catalyst Screen in Water

A modification of this general reaction procedure was then applied to the following reaction scheme, the results of the catalyst screen in water are presented in Table 2A below.

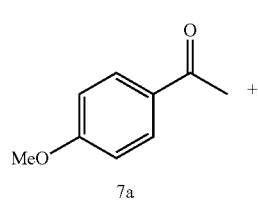

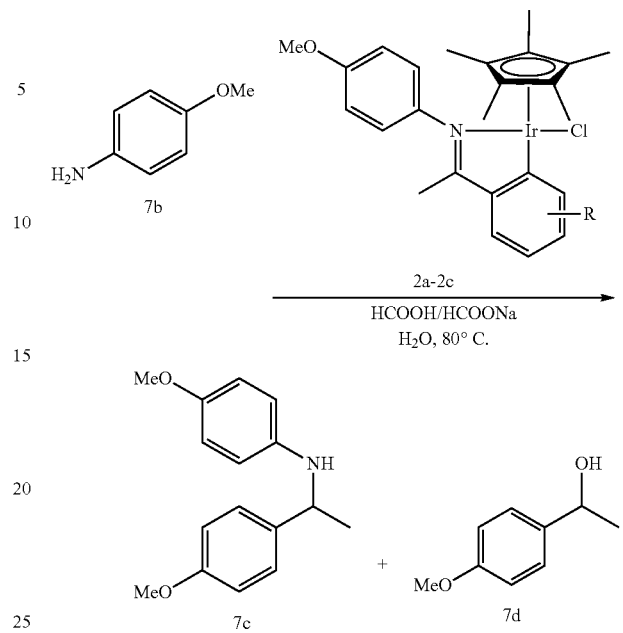

TABLE 2A

Catalyst Screening in Water

| Catalyst | R | T [min] | Conv.[b] [%] | 7c[b] [%] | 7d[b] [%] |
|---|---|---|---|---|---|
| 2b | p-OMe | 90 | 76 | 73 | 3 |
| 2a | p-CN | 90 | 17 | 17 | 0 |
| 2c | 4,5-(CH)₄ | 90 | 87 | 82 | 5 |
| 2c[c] | 4,5-(CH)₄ | 120 | 99 | 96 (95) | 3 |

[a]Reaction conditions: acetophenone (2.5 mmol), p-anisidine (3 mmol), catalyst (0.025 mmol), HCOOH/HCOONa solution (pH 4.8, 4 mL), 80° C., solution bubbled with argon for 15 min in a sealed tube.
[b]Determined by ¹H NMR spectroscopy.
[c]Acetophenone (2.5 mmol) and p-anisidine (5 mmol).
Number in brackets refers to the yield of the isolated product.

Solvent Screening for Catalyst Compound 2c

This general reaction procedure was then applied to the following reaction scheme, the results of the solvent screen for catalyst 2c being presented in Table 3 below.

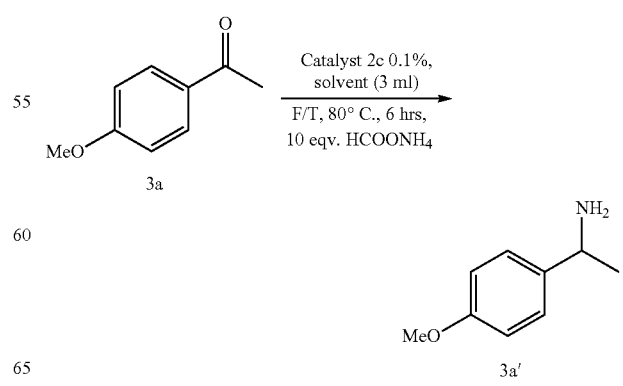

TABLE 3

Solvent screening for catalyst 2c

| Solvent | Conversion (%) |
| --- | --- |
| MeOH | 96 |
| EtOH | 92 |
| TFE | 8 |
| Toluene | 14 |
| DMF | 12 |

Range of Reductive Aminations with Catalyst Compound 2c

This general reaction procedure was then applied to the following reductive amination reactions using catalyst 2c in methanol, the results for which are presented in Table 4A below.

TABLE 4A reductive aminations of aromatic ketones with ammonium formate $$R_1 \text{-} \text{Ar-C(O)} R_2 + HCO_2NH_4 \xrightarrow[\text{overnight, 80°C}]{\text{2c (0.1 mol\%)}\atop\text{F/T, MeOH}} R_1 \text{-} \text{Ar-CH(NH}_2\text{)} R_2$$

| Ketones | Amines | Yield (%)[b] |
| --- | --- | --- |
| 2-acetylnaphthalene | 1-(naphth-2-yl)ethylamine | 93 |
| 6-methoxy-2-acetylnaphthalene | 1-(6-methoxynaphth-2-yl)ethylamine | 94 |
| acetophenone | 1-phenylethylamine | 84 |
| 4-phenylacetophenone | 1-(biphenyl-4-yl)ethylamine | 91 |
| 4'-methoxyacetophenone | 1-(4-methoxyphenyl)ethylamine | 88 |

TABLE 4A-continued reductive aminations of aromatic ketones with ammonium formate $$R_1 \text{-} \text{Ar-C(O)} R_2 + HCO_2NH_4 \xrightarrow[\text{overnight, 80°C}]{\text{2c (0.1 mol\%)}\atop\text{F/T, MeOH}} R_1 \text{-} \text{Ar-CH(NH}_2\text{)} R_2$$

| Ketones | Amines | Yield (%)[b] |
| --- | --- | --- |
| 4'-fluoroacetophenone | 1-(4-fluorophenyl)ethylamine | 89 |
| 4'-bromoacetophenone | 1-(4-bromophenyl)ethylamine | 91 |
| 4'-(trifluoromethyl)acetophenone | 1-(4-(trifluoromethyl)phenyl)ethylamine | 85 |
| 4'-nitroacetophenone | 1-(4-nitrophenyl)ethylamine | 90 |
| 3'-methoxyacetophenone | 1-(3-methoxyphenyl)ethylamine | 89 |
| 3'-fluoroacetophenone | 1-(3-fluorophenyl)ethylamine | 90 |

TABLE 4A-continued reductive aminations of aromatic ketones with ammonium formate

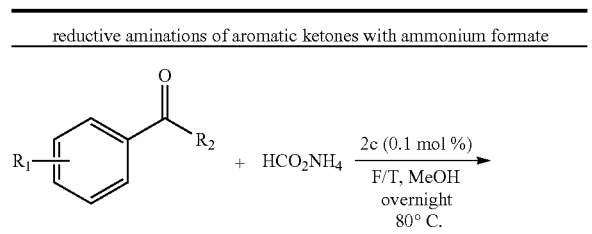

| Ketones | Amines | Yield (%)[b] |
|---|---|---|
| 3-bromoacetophenone | 1-(3-bromophenyl)ethylamine | 87 |
| 3-(trifluoromethyl)acetophenone | 1-(3-(trifluoromethyl)phenyl)ethylamine | 82 |
| 3-nitroacetophenone | 1-(3-nitrophenyl)ethylamine | 88 |
| 2-methoxyacetophenone | 1-(2-methoxyphenyl)ethylamine | 84 |
| 2-fluoroacetophenone | 1-(2-fluorophenyl)ethylamine | 86 |
| 3,4-dimethoxyacetophenone | 1-(3,4-dimethoxyphenyl)ethylamine | 90 |

TABLE 4A-continued reductive aminations of aromatic ketones with ammonium formate

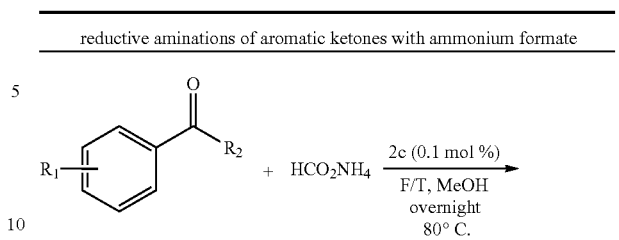

| Ketones | Amines | Yield (%)[b] |
|---|---|---|
| 3,4-methylenedioxyacetophenone | 1-(3,4-methylenedioxyphenyl)ethylamine | 92 |
| propiophenone | 1-phenylpropylamine | 88 |
| chalcone | 1,3-diphenylpropylamine | 82 |
| 1-indanone | 1-aminoindane | 90 |
| 1-tetralone | 1-amino-1,2,3,4-tetrahydronaphthalene | 87 |
| 2-acetylbenzofuran | 1-(benzofuran-2-yl)ethylamine | 91 |
| 3-acetyl-2,5-dimethylthiophene | 1-(2,5-dimethylthiophen-3-yl)ethylamine | 92 |

[a] Reaction conditions: ketone (0.5 mmol), HCO$_2$NH$_4$ (5 mmol), catalyst (5 × 10$^{-4}$ mmol), HCO$_2$H/Et$_3$N (5:2) azeotrope (0.5 ml), MeOH (3 ml) refluxed at 80° C. in a carousel tube, overnight.
[b] Yield of isolated product.

Further Reductive Aminations with Catalyst Compound 2c in Methanol

This general reaction procedure was then applied to the following reductive amination reactions using catalyst 2c in methanol, the results for which are presented in Table 4B below.

TABLE 4B reductive aminations of aliphatic ketones with ammonium formate $$R_1\text{-CO-}R_2 + HCO_2NH_4 \xrightarrow[\substack{\text{F/T, MeOH} \\ \text{overnight} \\ 80° C.}]{2c\ (0.1\ \text{mol}\ \%)} R_1\text{-CH(NH}_2\text{)-}R_2$$

| Ketones | Amines | Yield (%)[b] |
|---|---|---|
| PhCH₂CH₂C(O)CH₃ | PhCH₂CH₂CH(NH₂)CH₃ | 91 |
| 3,4-methylenedioxyphenyl-CH₂CH₂C(O)CH₃ | 3,4-methylenedioxyphenyl-CH₂CH₂CH(NH₂)CH₃ | 93 |
| 3-methylcyclohexanone | 3-methylcyclohexylamine | 84 |
| cyclohexyl-C(O)CH₃ | cyclohexyl-CH(NH₂)CH₃ | 83 |
| bicyclic ketone | bicyclic amine | 90 |

TABLE 4B-continued reductive aminations of aliphatic ketones with ammonium formate $$R_1\text{-CO-}R_2 + HCO_2NH_4 \xrightarrow[\substack{\text{F/T, MeOH} \\ \text{overnight} \\ 80° C.}]{2c\ (0.1\ \text{mol}\ \%)} R_1\text{-CH(NH}_2\text{)-}R_2$$

| Ketones | Amines | Yield (%)[b] |
|---|---|---|
| 2-octanone | 2-aminooctane | 82 |
| 2-nonanone | 2-aminononane | 84 |
| 6-methyl-5-hepten-2-one | 6-methyl-5-hepten-2-amine | 86 |
| dioxaspiro ketone | dioxaspiro amine | 90 |
| β-tetralone | 2-aminotetralin | 87 |

[a] Reaction conditions: ketone (0.5 mmol), HCO$_2$NH$_4$ (5 mmol), catalyst (5 × 10$^{-4}$ mmol), HCO$_2$H/Et$_3$N (5:2) azeotrope (0.5 ml), MeOH (3 ml) refluxed at 80° C. in a carousel tube, overnight.
[b] Yield of isolated product.

Further Reductive Aminations with Catalyst Compound 2c in Methanol

This general reaction procedure was then applied to the following reductive amination reactions using catalyst 2c in methanol, the results for which are presented in Table 4C below.

TABLE 4C reductive aminations of α-keto ethers with ammonium formate $$R_1\underset{\underset{}{}}{\overset{O}{\|}}\!\!\diagdown\!\!O\!\!\diagdown\!\! R_2 + HCO_2NH_4 \xrightarrow[\substack{F/T, MeOH \\ overnight \\ 80° C.}]{2c\ (0.1\ mol\ \%)} R_1\underset{\underset{}{NH_2}}{|}\!\!\diagdown\!\!O\!\!\diagdown\!\! R_2$$

| Ketones | Amines | Yield (%)[b] |
|---|---|---|
| CH₃C(O)CH₂O-Ph | CH₃CH(NH₂)CH₂O-Ph | 87 |
| CH₃C(O)CH₂O-(2,6-diMe-Ph) | CH₃CH(NH₂)CH₂O-(2,6-diMe-Ph) | 91 |
| PhC(O)CH₂O-(2,6-diMe-Ph) | PhCH(NH₂)CH₂O-(2,6-diMe-Ph) | 93 |
| PhC(O)CH₂O-(4-Cl-Ph) | PhCH(NH₂)CH₂O-(4-Cl-Ph) | 90 |
| PhC(O)CH₂O-(4-OMe-Ph) | PhCH(NH₂)CH₂O-(4-OMe-Ph) | 91 |
| PhC(O)CH₂OCH₂CF₃ | PhCH(NH₂)CH₂OCH₂CF₃ | 74 |
| PhC(O)CH₂OCH(CF₃)₂ | PhCH(NH₂)CH₂OCH(CF₃)₂ | 77 |
| 2-ethoxycyclohexanone | 2-ethoxycyclohexanamine | 81 |

[a] Reaction conditions: ketone (0.5 mmol), HCO₂NH₄ (5 mmol), catalyst (5 × 10⁻⁴ mmol), HCO₂H/Et₃N (5:2) azeotrope (0.5 ml), MeOH (3 ml) refluxed at 80° C. in a carousel tube, overnight.
[b]Yield of isolated product.

Further Reductive Aminations with Catalyst Compound 2c in Methanol

This general reaction procedure was then applied to the following reductive amination reactions using catalyst 2c in methanol, the results for which are presented in Table 4D below.

TABLE 4D reductive aminations of α-keto acids with ammonium formate $$R_1\text{-CO-CO-OH} + HCO_2NH_4 \xrightarrow[\substack{\text{F/T, MeOH} \\ \text{overnight} \\ 80°\text{C.}}]{2c\ (0.1\ \text{mol}\ \%)} R_1\text{-CH(NH}_2\text{)-COOH}$$

| Ketones | Amines | Yield (%)[b] |
|---|---|---|
| PhCO-COOH | PhCH(NH₂)-COOH | 95 |
| 4-Cl-C₆H₄-CO-COOH | 4-Cl-C₆H₄-CH(NH₂)-COOH | 91 |
| 4-F₃C-C₆H₄-CO-COOH | 4-F₃C-C₆H₄-CH(NH₂)-COOH | 90 |
| 4-MeO-C₆H₄-CO-COOH | 4-MeO-C₆H₄-CH(NH₂)-COOH | 88 |
| 2-Naphthyl-CO-COOH | 2-Naphthyl-CH(NH₂)-COOH | 96 |
| 3-Indolyl-CO-COOH | 3-Indolyl-CH(NH₂)-COOH | 94 |
| 2-Thienyl-CO-COOH | 2-Thienyl-CH(NH₂)-COOH | 92 |

[a] Reaction conditions: ketone (0.5 mmol), HCO₂NH₄ (5 mmol), catalyst (5 × 10⁻⁴ mmol), HCO₂H/Et₃N (5:2) azeotrope (0.5 ml), MeOH (3 ml) refluxed at 80° C. in a carousel tube, overnight.
[b] Yield of isolated product.

Further Reductive Aminations with Catalyst Compound 2c in Water

A modification of this general reaction procedure was then applied to the following reductive amination reactions using catalyst 2c in water, the results for which are presented in Table 4E below.

TABLE 4E reductive aminations of aromatic ketones with sodium formate at pH 4.8

$$\text{R} \overset{}{\underset{}{\diagdown}} \text{C(O)R'} + \text{R''}-\text{NH}_2 \xrightarrow[\text{H}_2\text{O, 80°C. pH 4.8}]{\text{catalyst 2c} \atop \text{HCOOH/HCOONa}} \text{R} \overset{}{\underset{}{\diagdown}} \text{CH(NHR'')R'}$$

| Entry[a] | Ketone | Amine | S/C | r[h] | Yield [%][b] |
|---|---|---|---|---|---|
| 1 | acetophenone | 4-methoxyaniline | 1000 | 2 | 95 |
| 2 | 4'-methylacetophenone | 4-methoxyaniline | 1000 | 2 | 98 |
| 3 | 4'-methoxyacetophenone | 4-methoxyaniline | 1000 | 2 | 95 |
| 4 | 4'-fluoroacetophenone | 4-methoxyaniline | 1000 | 2 | 94 |
| 5 | 4'-chloroacetophenone | 4-methoxyaniline | 1000 | 2 | 98 |
| 6 | 4'-bromoacetophenone | 4-methoxyaniline | 1000 | 2 | 98 |
| 7 | 4'-cyanoacetophenone | 4-methoxyaniline | 1000 | 2 | 98 |
| 8 | 4'-(trifluoromethyl)acetophenone | 4-methoxyaniline | 1000 | 2 | 96 |

TABLE 4E-continued reductive aminations of aromatic ketones with sodium formate at pH 4.8

$$R\underset{\Vert}{\overset{O}{-}}\!\!\!\!\!\!\!\!\!\!\!\!\!\!\!\!\!\!\!\!\!\!\!\!-\!\!\!-\!\!\!\!-\!\!\!\!C(=O)R' + R''-NH_2 \xrightarrow[\substack{HCOOH/HCOONa \\ H_2O, 80° C. \\ pH 4.8}]{catalyst\ 2c} R-\text{Ar}-CH(NHR'')R'$$

| Entry[a] | Ketone | Amine | S/C | r[h] | Yield [%][b] |
|---|---|---|---|---|---|
| 9 | 4-O$_2$N-C$_6$H$_4$-C(=O)CH$_3$ | 4-MeO-C$_6$H$_4$-NH$_2$ | 1000 | 2 | 93 |
| 10 | 2-naphthyl-C(=O)CH$_3$ | 4-MeO-C$_6$H$_4$-NH$_2$ | 1000 | 2 | 92 |
| 11[c] | PhC(=O)CH$_2$C(=O)OMe | 4-MeO-C$_6$H$_4$-NH$_2$ | 200 | 12 | 71 |
| 12 | PhC(=O)CH$_3$ | PhNH$_2$ | 1000 | 2 | 82 |
| 13 | PhC(=O)CH$_3$ | 4-Me-C$_6$H$_4$-NH$_2$ | 1000 | 2 | 91 |
| 14 | PhC(=O)CH$_3$ | 4-F-C$_6$H$_4$-NH$_2$ | 1000 | 2 | 93 |
| 15 | PhC(=O)CH$_3$ | 4-Cl-C$_6$H$_4$-NH$_2$ | 1000 | 10 | 77 |
| 16 | PhC(=O)CH$_3$ | 4-Br-C$_6$H$_4$-NH$_2$ | 200 | 24 | 59 |

TABLE 4E-continued reductive aminations of aromatic ketones with sodium formate at pH 4.8

R-[benzene ring]-C(=O)-R' + R''-NH₂ →(catalyst 2c, HCOOH/HCOONa, H₂O, 80° C., pH 4.8)→ R-[benzene ring]-CH(NHR'')-R'

| Entry[a] | Ketone | Amine | S/C | r[h] | Yield [%][b] |
|---|---|---|---|---|---|
| 17 | acetophenone | benzylamine (H₂N-CH₂-Ph) | 2000 | 4 | 87 |
| 18 | acetophenone | H₂N-(CH₂)₆- | 200 | 64 | 82 |
| 19 | acetophenone | phenylalanine methyl ester | 500 | 24 | 44 (>99.2)[d] |

[a]Reaction conditions: ketone (2.5 mmol), amine (5 mmol) 2c HCOOH/HCOONa solution (pH 4.8, 4 mL), 80° C.
[b]Yield of the isolated product.
[c]pH 4.2.
[d]The diastereomeric ratio (d.r.) is given in brackets.

Further Reductive Aminations with Catalyst Compound 2c in Water

A modification of this general reaction procedure was then applied to the following reductive amination reactions using catalyst 2c in water, the results for which are presented in Table 4F below.

TABLE 4F reductive aminations of aliphatic ketones with sodium formate at pH 4.8

R-C(=O)-R + R''-NH(R') →(catalyst 2c, HCOOH/HCOONa, H₂O, 80° C., pH 4.8)→ R-CH(N(R'')(R'))-

| Entry[a] | Ketone | Amine | S/C | r[h] | Yield [%][b] |
|---|---|---|---|---|---|
| 1 | Ph-CH₂-CH₂-C(=O)-CH₃ | 4-methoxyaniline (H₂N-C₆H₄-OCH₃) | 2000 | 2 | 98 |

TABLE 4F-continued reductive aminations of aliphatic ketones with sodium formate at pH 4.8

$$\underset{R}{\overset{O}{\|}}\!\!-\!\!R' + R''\!\!-\!\!\underset{H}{\overset{R'}{N}}\!\!H \xrightarrow[\substack{HCOOH/HCOONa \\ H_2O,\ 80°\ C. \\ pH\ 4.8}]{catalyst\ 2c} \underset{R}{\overset{R''\underset{}{\diagdown}N\underset{}{\diagup}R'}{\|}}$$

| Entry[a] | Ketone | Amine | S/C | r[h] | Yield [%][b] |
|---|---|---|---|---|---|
| 2 | PhCH₂CH₂C(O)CH₃ | aniline | 2000 | 2 | 99 |
| 3 | PhCH₂CH₂C(O)CH₃ | 4-methylaniline | 2000 | 2 | 98 |
| 4 | PhCH₂CH₂C(O)CH₃ | 4-fluoroaniline | 2000 | 2 | 98 |
| 5 | PhCH₂CH₂C(O)CH₃ | 4-chloroaniline | 2000 | 2 | 99 |
| 6 | PhCH₂CH₂C(O)CH₃ | 4-bromoaniline | 1000 | 2 | 96 |
| 7 | PhCH₂CH₂C(O)CH₃ | 4-(trifluoromethyl)aniline | 2000 | 2 | 79 |
| 8 | PhCH₂CH₂C(O)CH₃ | benzylamine | 2000 | 2 | 97 |
| 9 | PhCH₂CH₂C(O)CH₃ | H₂N(CH₂)₁₀- | 2000 | 2 | 54 |

TABLE 4F-continued reductive aminations of aliphatic ketones with sodium formate at pH 4.8

$$R-\overset{O}{\underset{}{C}}-R + R''-\overset{R'}{\underset{H}{N}}H \xrightarrow[\substack{HCOOH/HCOONa \\ H_2O,\ 80°\ C. \\ pH\ 4.8}]{\text{catalyst 2c}} R-\overset{R''\underset{}{N}R'}{\underset{}{C}}H$$

| Entry[a] | Ketone | Amine | S/C | r[h] | Yield [%][b] |
|---|---|---|---|---|---|
| 10 | PhCH₂CH₂C(O)CH₃ | H₂N(CH₂)₆CH₃ | 1000 | 6 | 85 |
| 11[c] | PhCH₂CH₂C(O)CH₃ | cyclohexyl-NH₂ | 200 | 48 | 52 |
| 12[c] | PhCH₂CH₂C(O)CH₃ | PhNH(CH₃) | 200 | 24 | 64 |
| 13 | PhCH₂CH₂C(O)CH₃ | D-Phe-OMe | 2000 | 3 | 95 (=79:21)[d] |
| 14 | PhCH=CHC(O)CH₃ | 4-MeO-C₆H₄-NH₂ | 1000 | 4 | 93 |
| 15 | acetone | 4-MeO-C₆H₄-NH₂ | 1000 | 2 | 98 |
| 16 | CH₃C(O)(CH₂)₂CH₃ | 4-MeO-C₆H₄-NH₂ | 2000 | 2 | 88 |
| 17 | CH₃C(O)(CH₂)₅CH₃ | 4-MeO-C₆H₄-NH₂ | 2000 | 2 | 98 |
| 18 | cyclohexanone | 4-MeO-C₆H₄-NH₂ | 2000 | 2 | 95 |

TABLE 4F-continued reductive aminations of aliphatic ketones with sodium formate at pH 4.8

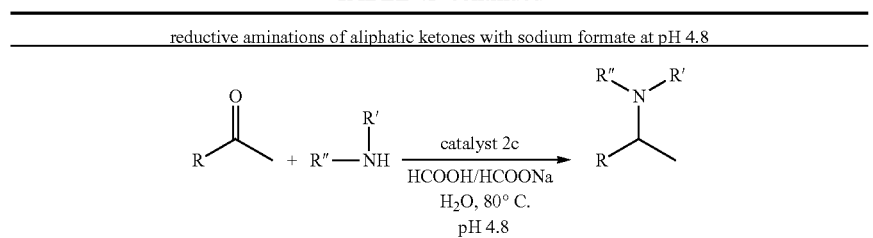

| Entry[a] | Ketone | Amine | S/C | r[h] | Yield [%][b] |
|---|---|---|---|---|---|

[a]Reaction conditions: ketone (5 mmol), amine (10 mmol), 2c HCOOH/HCOONa solution (pH 4.8, 8 mL), 80° C.
[b]Yield of the isolated product.
[c]pH 5.0.
[d]The d.r. value is given in brackets.

Further Reductive Aminations with Catalyst Compound 2c in Water

A modification of this general reaction procedure was then applied to the following reductive amination reactions using catalyst 2c in water, the results for which are presented in Table 4G below.

TABLE 4G reductive aminations of various aldehydes with sodium formate at pH 4.8

| Entry[a] | Aldehyde | Amine | S/C | r[h] | Yield [%][b] |
|---|---|---|---|---|---|
| 1 | benzaldehyde | 4-methoxyaniline | 2000 | 2 | 98 |
| 2 | 4-methylbenzaldehyde | 4-methoxyaniline | 2000 | 2 | 98 |
| 3 | 4-methoxybenzaldehyde | 4-methoxyaniline | 2000 | 2 | 95 |
| 4 | 4-fluorobenzaldehyde | 4-methoxyaniline | 2000 | 2 | 97 |
| 5 | 4-chlorobenzaldehyde | 4-methoxyaniline | 2000 | 2 | 79 |

TABLE 4G-continued reductive aminations of various aldehydes with sodium formate at pH 4.8

$$R-CHO + R''-NH-R' \xrightarrow[\substack{HCOOH/HCOONa \\ H_2O,\ 80°\ C. \\ pH\ 4.8}]{catalyst\ 2c} R-CH_2-N(R')(R'')$$

| Entry[a] | Aldehyde | Amine | S/C | r[h] | Yield [%][b] |
|---|---|---|---|---|---|
| 6 | 4-Br-C6H4-CHO | 4-MeO-C6H4-NH2 | 2000 | 2 | 92 |
| 7 | 3-Br-C6H4-CHO | 4-MeO-C6H4-NH2 | 2000 | 2 | 97 |
| 8 | 4-F3C-C6H4-CHO | 4-MeO-C6H4-NH2 | 2000 | 2 | 96 |
| 9 | 4-O2N-C6H4-CHO | 4-MeO-C6H4-NH2 | 2000 | 4 | 97 |
| 10 | C6H5-CHO | C6H5-NH2 | 2000 | 5 | 97 |
| 11 | C6H5-CHO | 4-Me-C6H4-NH2 | 2000 | 2 | 94 |
| 12 | C6H5-CHO | 4-F-C6H4-NH2 | 2000 | 2 | 98 |
| 13 | C6H5-CHO | 4-Cl-C6H4-NH2 | 2000 | 2 | 99 |
| 14 | C6H5-CHO | 4-Br-C6H4-NH2 | 1000 | 2 | 95 |
| 15 | C6H5-CHO | C6H5-CH2-NH2 | 2000 | 2 | 96 |

TABLE 4G-continued reductive aminations of various aldehydes with sodium formate at pH 4.8

$$R-CHO + R''-NH-R' \xrightarrow[\substack{HCOOH/HCOONa \\ H_2O,\ 80°\ C. \\ pH\ 4.8}]{\text{catalyst 2c}} R-CH_2-N(R'')(R')$$

| Entry[a] | Aldehyde | Amine | S/C | r[h] | Yield [%][b] |
|---|---|---|---|---|---|
| 16 | benzaldehyde | H₂N-(CH₂)₆-CH₃ (octylamine) | 2000 | 2 | 97 |
| 17 | benzaldehyde | H₂N-(CH₂)₁₀-CH₃ (dodecylamine) | 1000 | 4 | 83 |
| 18 | benzaldehyde | cyclohexylamine | 1000 | 4 | 93 |
| 19 | benzaldehyde | N-methylaniline | 1000 | 5 | 72 |
| 20 | benzaldehyde | N-methylbenzylamine | 1000 | 2 | 98 |
| 21 | benzaldehyde | L-phenylalanine methyl ester | 500 | 2 | 99 |

[a]Reaction conditions: aldehydes (5 mmol), amine (10 mmol), 2c HCOOH/HCOONa solution (pH 4.8, 8 mL), 80° C.
[b]Yield of the isolated product.

Conclusion

The results show that the catalyst compounds of Formula I facilitate transfer hydrogenation reactions across a range of substrates and reaction conditions, though they are especially suitable for use in transfer hydrogenations where the reaction solvent is methanol or ethanol. FIG. 1 in particular demonstrates the superior catalytic activity of a compound of Formula I, specifically Example 2c, relative to comparative example 2b catalyst of the prior art.

EXAMPLES

Catalyst Compound of Formula A

Materials and Equipment

Unless otherwise specified, all reagents were commercially purchased from Aldrich, Alfa Aesar, Acros organics, Apollo scientific, or Fluorochem and used without further purification. Molecular sieves (4 Å) were heated in oven at 160° C. overnight prior to use. NMR spectra were recorded on a Brucker 400 MHz NMR spectrometer with TMS as an internal standard, all at ambient temperature.

Example 4

General Procedures for Preparation of Imine Ligands

Ketone (10 mmol), amine (10 mmol) and activated 4 Å molecular sieves (2 g) were introduced in a Smith Process Vial™ containing a small stirrer bar. The vial was then degassed and recharged with nitrogen gas for three times. The vial was sealed and heated with a microwave reactor at 200° C. for 3-6 hours. The desired imine was purified by recrystallization from hexane and DCM.

Example 5

General Procedures for Preparation of Cyclometalated Complexes

[Cp*IrCl₂]₂ (1 equiv.), an imine ligand (2.2 equiv.) and NaOAc (10 equiv.) were placed into a Schlenk tube. The tube was then degassed and recharged with nitrogen gas for three times. DCM was then added and the resulting mixture was stirred at room temperature overnight. The reaction mixture was filtered through celite, and dried over MgSO4. Following removal of the solvent under vacuum the resulting solid was washed with diethyl ether.

Specific examples are now described.

Example 5a

Preparation of (E)-N-(3,4-dihydronaphthalen-1(2H)-ylidene)-4-methoxyaniline iridium complex 5a (p-methoxyphenyl/tetralone derivative)

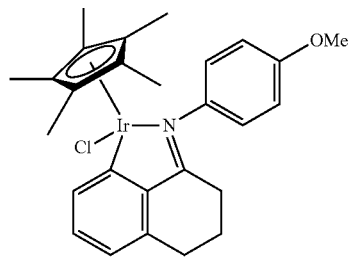

5a

The product was obtained as an orange powder (90.5 mg, 98%) according to the general procedure for the preparation of cyclometalated complexes from [Cp*IrCl$_2$]$_2$ and (E)-N-(3,4-dihydronaphthalen-1(2H)-ylidene)-4-methoxyaniline. $^1$H NMR (CDCl$_3$, 400 MHz, 258K) δ 7.82 (m, 1H), 7.66 (d, 1H), 7.17 (t, 1H), 6.99-6.92 (m, 3H), 6.80 (d, 1H), 3.88 (s, 3H), 3.01-2.66 (m, 4H), 1.91-1.90 (m, 2H), 1.46 (s 15H) ppm; $^{13}$C NMR (CDCl3, 100 MHz, 258K) δ 182.9, 168.4, 157.4, 144.6, 143.4, 143.0, 132.7, 132.4, 125.2, 123.3, 121.2, 115.0, 112.3, 88.9, 55.7, 30.4, 29.2, 23.8, 15.5, 8.9 ppm; Analytical calculation for C$_{27}$H$_{31}$ClIrNO (%): C, 52.88; H, 5.10; N, 2.61. Found: C, 52.69; H, 5.12; N, 2.09.

Example 5b

Preparation of (E)-4-methoxy-N-(6-methoxy-3,4-dihydronaphthalen-1(2H)-ylidene)aniline iridium complex 5b (p-methoxyphenyl/p-methoxyphenyl tetralone derivative)

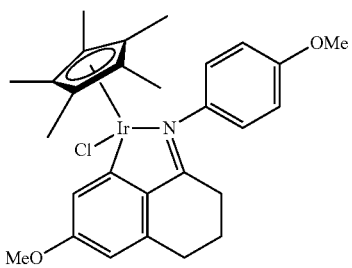

5b

The product was obtained as a light orange powder (31.7 mg, 98%) according to the general procedure for the preparation of cyclometalated complexes from [Cp*IrCl$_2$]$_2$ and (E)-4-methoxy-N-(6-methoxy-3,4-dihydronaphthalen-1(2H)-ylidene)aniline. $^1$H NMR (CDCl$_3$, 400 MHz, 258K) δ 7.82-7.80 (m, 1H), 7.19 (s, 1H), 6.97-6.86 (m, 3H), 6.37 (s, 1H), 3.91 (s, 3H), 3.87 (s, 3H), 2.96-2.60 (m, 4H), 1.89-1.88 (m, 2H) ppm; $^{13}$C NMR (CDCl3, 100 MHz) δ 181.4, 170.7, 162.3, 157.5, 144.7, 143.5, 138.4, 124.8, 117.6, 114.2, 113.8, 113.5, 106.9, 88.7, 55.6, 55.0, 30.2, 29.5, 23.9. 8.7 ppm; Analytical calculation for C$_{28}$H$_{33}$ClIrNO$_2$%: C, 52.28; H, 5.17; N, 2.18. Found: C, 52.43; H, 5.48; N, 1.94.

Example 6

General Procedure for Hydrogenation of Imine

The imine (0.3 mmol) was added to a 3 ml glass tube equipped with a magnetic stirrer bar. Then 0.5 ml of trifluoroethanol was added, and a solution of the catalyst compound in trifluoroethanol (3×10$^{-5}$ mmol) was transferred into the tube with syringe. The tube was put into a stainless steel autoclave and the gas was exchanged with hydrogen for three times. The reaction was carried out in one hour with 20 bar pressure at 85° C. The autoclave was cooled down to room temperature after reaction and hydrogen gas was released slowly. The solvent was removed under the reduced pressure and the product was purified by a short silica gel column using petroleum ether and ethyl acetate as eluent.

The following experiments have been performed, by way of example, to illustrate the applicability of the present invention.

Range of Reductions with Catalyst Compounds 5a and 5b

This general reaction procedure was then applied to the following reductive amination reactions using catalysts 5a and 5b in trifluoroethanol (TFE), the results for which are presented in Table 5 below.

TABLE 5

Hydrogenation of imines (6) with high substrate to catalyst (S/C) ratios using catalysts 5a and 5b in TFE

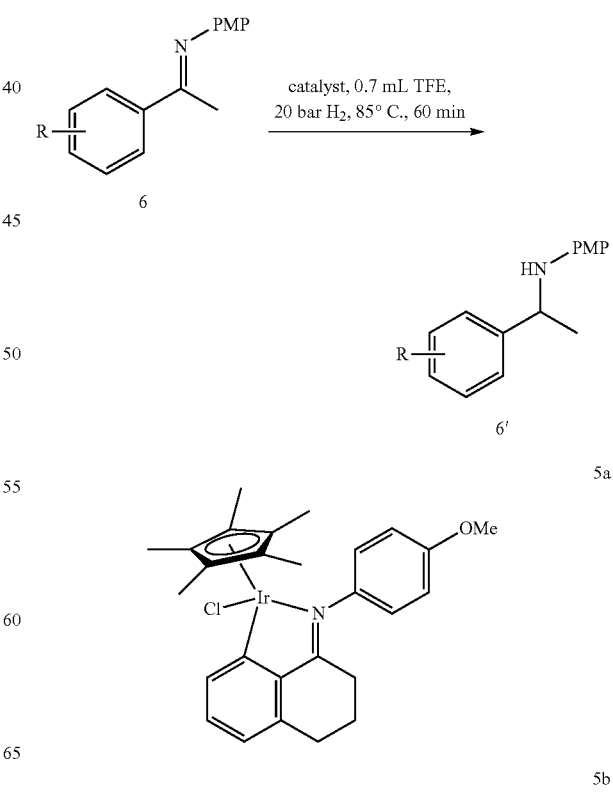

TABLE 5-continued

[Catalyst structure: pentamethylcyclopentadienyl Ir complex with Cl and N-(4-methoxyphenyl)imine ligand from methoxy-substituted tetrahydronaphthalenone]

| Entry | Product | S/C | Yield (%)[b] |
|---|---|---|---|
| 1 | 6a' (N-(1-phenylethyl)-4-methoxyaniline) | 10000 | 90 / 70[c] |
| 2 | 6b' (N-(1-(4-methylphenyl)ethyl)-4-methoxyaniline) | 10000 | 90 |
| 3 | 6c' (N-(1-(4-nitrophenyl)ethyl)-4-methoxyaniline) | 10000 / 1000 | 11 / 90 |
| 4 | 6d' (N-(1-(3,4-dimethoxyphenyl)ethyl)-4-methoxyaniline) | 10000 | 91 |
| 5 | 6g' (N-(1-(3-nitrophenyl)ethyl)-4-methoxyaniline) | 1000 | 91 |
| 6 | 6t' (N-(1-(4-chlorophenyl)ethyl)-4-methoxyaniline) | 10000 | 91 |
| 7 | 6u' (N-(1-(3-methylphenyl)ethyl)-4-methoxyaniline) | 10000 | 90 |
| 8 | 6v' (N-(1-(4-isobutylphenyl)ethyl)-4-methoxyaniline) | 10000 | 88 |
| 9 | 6w' (N-(1-(naphthalen-2-yl)ethyl)-4-methoxyaniline) | 10000 | 89 |

TABLE 5-continued

| # | Structure | | |
|---|---|---|---|
| 10 | 6x' (HN-CH(CH3)-Ph, Ar = 4-Br-C6H4) | 10000 1000 | 45 91 |
| 11 | 6y' (HN-CH(CH3)-(4-Br-C6H4), Ar = 4-OMe-C6H4) | 10000 2000 | 53 91 |

[a] Reaction conditions: 0.3 mmol of imine, 0.1-0.01 mol % catalyst 5a, 0.5 mL CF$_3$CH$_2$OH, 20 bar H$_2$, 85° C., 60 min.
[b] Isolated yields.
[c] 0.01 mol % catalyst 5b was used.

Conclusion

The results show that the catalyst compounds of Formula A facilitate hydrogenation reactions across a range of substrates and reaction conditions.

The invention claimed is:

1. A catalyst compound, wherein the catalyst compound is defined by the Formula I:

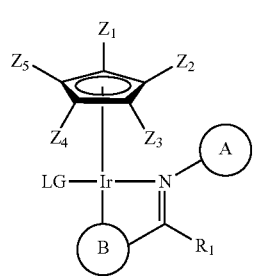

Formula I wherein:
ring A of the Formula I is aryl or heteroaryl, optionally substituted by one or two groups selected from the group consisting of hydroxyl, NR$^a$R$^b$, (1-6C)alkyl, (1-6C)alkoxy, and aryl which is optionally substituted by halogeno, hydroxyl, NR$^a$R$^b$, (1-6C)alkyl, or (1-6C)alkoxy, wherein R$^a$ and R$^b$ are each independently hydrogen or (1-6C)alkyl;
ring B of the Formula I is a bicyclic or tricyclic aromatic or heteroaromatic fused ring system, optionally substituted by one or more groups selected from the group consisting of halogeno, hydroxyl, NR$^c$R$^d$, (1-6C)alkyl, (1-6C)alkoxy, [NR$^c$R$^d$R$^e$]$^+$, nitro, cyano, formyl, carboxy, carbamoyl, sulphamoyl, ureido, isocyano, sulphonyl, sulphonate, trihalomethyl, and mercapto, wherein R$^c$, R$^d$, and R$^e$ are each independently hydrogen, (1-6C)alkyl or aryl, or a group of the formula:

$$L_1-Q_1$$

wherein:
L$_1$ is absent or is selected from the group consisting of O, S, SO, SO$_2$, N(R$^f$), C(O), CH(OR$^f$), C(O)N(R$^f$), N(R$^f$)C(O), N(R$^f$)C(O)N(R$^g$), S(O)$_2$N(R$^f$), and N(R$^f$)SO$_2$, wherein R$^f$ and R$^g$ are each independently hydrogen or (1-4C)alkyl; and
Q$_1$ is (1-6C)alkyl, (2-6C)alkenyl, (2-6C)alkynyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; wherein Q$_1$ is optionally further substituted by one or more substituents each independently selected from the group consisting of halogeno, hydroxyl, NR$^c$R$^d$, [NR$^c$R$^d$R$^e$]$^+$, (1-6C)alkyl, (1-6C)alkoxy, nitro, cyano, formyl, carboxy, carbamoyl, ureido, isocyano, sulphonyl, sulphonate, trifluoromethyl, and mercapto;
R$_1$ of the Formula I is selected from the group consisting of hydrogen, (1-6C)alkyl, (2-6C)alkenyl, (2-6C)alkynyl, aryl, (3-6C)cycloalkyl and heteroaryl; or R$_1$ is (2-4C)alkylene or (2-4C)alkenylene linked to ring B to form a fused 5-, 6- or 7-membered ring, wherein R$_1$ is optionally substituted by one or more groups selected from the group consisting of halogeno, hydroxyl, NR$^h$R$^i$, (1-6C)alkyl, (1-6C)alkoxy, [NR$^h$R$^i$R$^j$]$^+$, nitro, cyano, formyl, carboxy, carbamoyl, sulphamoyl, ureido, isocyano, sulphonyl, sulphonate, trihalomethyl, and mercapto, wherein R$^h$, R$^i$, and R$^j$ are each independently hydrogen, (1-6C)alkyl or aryl, or a group of the formula:

$$L_2-Q_2$$

wherein:
L$_2$ is absent or is selected from the group consisting of O, S, SO, SO$_2$, N(R$^k$), C(O), CH(OR$^k$), C(O)N(R$^k$), N(R$^k$)C(O), N(R$^k$)C(O)N(R$^l$), S(O)$_2$N(R$^k$), and N(R$^k$)SO$_2$, wherein R$^k$ and R$^l$ are each independently hydrogen or (1-4C)alkyl; and
Q$_2$ is (1-6C)alkyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; wherein Q$_2$ is optionally further substituted by one or more substituents each independently selected from the group consisting of halogeno, hydroxyl, NR$^m$R$^n$, [NR$^m$R$^n$R$^o$]$^+$, (1-6C)alkyl, (1-6C)alkoxy, nitro, cyano, formyl, carboxy, carbamoyl, ureido, isocyano, sulphonyl, sulphonate, trifluoromethyl, and mercapto, wherein R$^m$, R$^n$, and R$^o$ are each independently hydrogen, (1-6C)alkyl or aryl;
LG of the Formula I is a leaving group;
Z$_1$, Z$_2$, Z$_3$, Z$_4$, and Z$_5$ of the Formula I are each independently selected from the group consisting of hydrogen, (1-6C)alkyl, aryl, (1-6C)alkoxy, hydroxyl, and NR$^p$R$^q$, wherein R$^p$ and R$^q$ are each independently hydrogen, (1-6C)alkyl or aryl;

or the catalyst compound is defined by the Formula A:

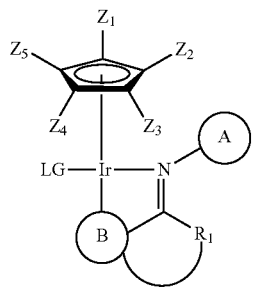

Formula A wherein:
ring A of the Formula A is aryl or heteroaryl, optionally substituted by one or two groups each independently selected from the group consisting of hydroxyl, $NR^aR^b$, (1-6C)alkyl, (1-6C)alkoxy, and aryl which is optionally substituted by halogeno, hydroxyl, $NR^aR^b$, (1-6C)alkyl or (1-6C)alkoxy, wherein $R^a$ and $R^b$ are each independently hydrogen or (1-6C)alkyl;
ring B of the Formula A is a aryl or heteroaryl, optionally substituted by one or more groups each independently selected from the group consisting of halogeno, hydroxyl, $NR^cR^d$, (1-6C)alkyl, (1-6C)alkoxy, $[NR^cR^dR^e]^+$, nitro, cyano, formyl, carboxy, carbamoyl, sulphamoyl, ureido, isocyano, sulphonyl, sulphonate, trihalomethyl, and mercapto, wherein $R^c$, $R^d$, and $R^e$ are each independently hydrogen, (1-6C)alkyl or aryl, or a group of the formula:

$L_1\text{-}Q_1$ wherein:
$L_1$ is absent or is selected from the group consisting of O, S, SO, $SO_2$, $N(R^f)$, C(O), $CH(OR^f)$, $C(O)N(R^f)$, $N(R^f)C(O)$, $N(R^f)C(O)N(R^g)$, $S(O)_2N(R^f)$, and $N(R^f)SO_2$, wherein $R^f$ and $R^g$ are each independently hydrogen or (1-4C)alkyl; and
$Q_1$ is (1-6C)alkyl, (2-6C)alkenyl, (2-6C)alkynyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; wherein $Q_1$ is optionally further substituted by one or more substituents each independently selected from the group consisting of halogeno, hydroxyl, $NR^cR^d$, $[NR^cR^dR^e]^+$, (1-6C)alkyl, (1-6C)alkoxy, nitro, cyano, formyl, carboxy, carbamoyl, ureido, isocyano, sulphonyl, sulphonate, trifluoromethyl and mercapto;
$R_1$ of the Formula A is (2-4C)alkylene or (2-4C)alkenylene linked to ring B to form a fused 5- 6-, or 7-membered ring, wherein $R_1$ is optionally substituted by one or more groups each independently selected from the group consisting of halogeno, hydroxyl, $NR^hR^i$, (1-6C)alkyl, (1-6C)alkoxy, $[NR^hR^iR^j]^+$, nitro, cyano, formyl, carboxy, carbamoyl, sulphamoyl, ureido, isocyano, sulphonyl, sulphonate, trihalomethyl and mercapto, wherein $R^h$, $R^i$, and $R^j$ are each independently hydrogen, (1-6C)alkyl or aryl, or a group of the formula:

$L_2\text{-}Q_2$ wherein:
$L_2$ is absent or is selected from the group consisting of O, S, SO, $SO_2$, $N(R^k)$, C(O), $CH(OR^k)$, $C(O)N(R^k)$, $N(R^k)C(O)$, $N(R^k)C(O)N(R^l)$, $S(O)_2N(R^k)$ and $N(R^k)SO_2$, wherein $R^k$ and $R^l$ are each independently hydrogen or (1-4C)alkyl; and
$Q_2$ is (1-6C)alkyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; wherein $Q_2$ is optionally further substituted by one or more substituents each independently selected from the group consisting of halogeno, hydroxyl, $NR^mR^n$, $[NR^mR^nR^o]^+$, (1-6C)alkyl, (1-6C)alkoxy, nitro, cyano, formyl, carboxy, carbamoyl, ureido, isocyano, sulphonyl, sulphonate, trifluoromethyl and mercapto, wherein $R^m$, $R^n$, and $R^o$ are each independently hydrogen, (1-6C)alkyl or aryl;
LG of the Formula A is a leaving group;
$Z_1$, $Z_2$, $Z_3$, $Z_4$, and $Z_5$ of the Formula A are each independently selected from the group consisting of hydrogen, (1-6C)alkyl, aryl, (1-6C)alkoxy, hydroxyl and $NR^pR^q$, wherein $R^p$ and $R^q$ are each independently hydrogen, (1-6C)alkyl or aryl.

2. The catalyst compound of claim 1, wherein ring A of the Formula I or ring A of the Formula A is phenyl, optionally substituted, in either or both of the ortho- or para-position relative to the imine nitrogen atom to which ring A is attached, by one or two groups each independently selected from the group consisting of hydroxyl, $NR^aR^b$, (1-3C)alkyl, (1-3C)alkoxy and aryl which is optionally substituted by halogeno, hydroxyl, $NR^aR^b$, (1-3C)alkyl or (1-3C)alkoxy, wherein $R^a$ and $R^b$ are each independently hydrogen or (1-2C)alkyl.

3. The catalyst compound of claim 1, wherein ring A of the Formula I or ring A of the Formula A is para-methoxyphenyl.

4. The catalyst compound of claim 1, wherein ring B of the Formula I is naphthyl, optionally substituted by one or more groups selected from the group consisting of halogeno, hydroxyl, $NR^cR^d$, (1-6C)alkyl, (1-6C)alkoxy, $[NR^cR^dR^e]^+$, nitro, cyano, formyl, carboxy, carbamoyl, sulphamoyl, ureido, isocyano, sulphonyl, sulphonate, trihalomethyl, and mercapto, wherein $R^c$, $R^d$, and $R^e$ are each independently hydrogen, (1-6C)alkyl or aryl, or a group of the formula:

$L_1\text{-}Q_1$ wherein:
$L_1$ is absent or is selected from the group consisting of O, S, SO, $SO_2$, $N(R^f)$, C(O), $CH(OR^f)$, $C(O)N(R^f)$, $N(R^f)C(O)$, $N(R^f)C(O)N(R^g)$, $S(O)_2N(R^f)$, and $N(R^f)SO_2$, wherein $R^f$ and $R^g$ are each independently hydrogen or (1-4C)alkyl; and
$Q_1$ is (1-6C)alkyl, (2-6C)alkenyl, (2-6C)alkynyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; wherein $Q_1$ is optionally further substituted by one or more substituents each independently selected from the group consisting of halogeno, hydroxyl, $NR^cR^d$, $[NR^cR^dR^e]^+$, (1-6C)alkyl, (1-6C)alkoxy, nitro, cyano, formyl, carboxy, carbamoyl, ureido, isocyano, sulphonyl, sulphonate, trifluoromethyl, and mercapto.

5. The catalyst compound of claim 1, wherein ring B of the Formula I is β,β-naphthyl, optionally substituted by one or more groups selected from the group consisting of halogeno, hydroxyl, $NR^cR^d$, (1-6C)alkyl, (1-6C)alkoxy, $[NR^cR^dR^e]^+$, nitro, cyano, formyl, carboxy, carbamoyl, sulphamoyl, ureido, isocyano, sulphonyl, sulphonate, trihalomethyl, and mercapto, wherein $R^c$, $R^d$, and $R^e$ are each independently hydrogen, (1-6C)alkyl or aryl, or a group of the formula:

$L_1\text{-}Q_1$ wherein:

L₁ is absent or is selected from the group consisting of O, S, SO, SO₂, N(R^f), C(O), CH(OR^f), C(O)N(R^f), N(R^f)C(O), N(R^f)C(O)N(R^g), S(O)₂N(R^f), and N(R^f)SO₂, wherein R^f and R^g are each independently hydrogen or (1-4C)alkyl; and Q₁ is (1-6C)alkyl, (2-6C)alkenyl, (2-6C)alkynyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; wherein Q₁ is optionally further substituted by one or more substituents each independently selected from the group consisting of halogeno, hydroxyl, $NR^cR^d$, $[NR^cR^dR^e]^+$, (1-6C)alkyl, (1-6C)alkoxy, nitro, cyano, formyl, carboxy, carbamoyl, ureido, isocyano, sulphonyl, sulphonate, trifluoromethyl, and mercapto;

such that the naphthyl substituent is attached to the iridium atom and imine-carbon atom respectively at the 2- and 3-position of the naphthyl ring, i.e. has the connectivity:

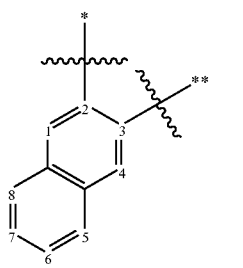

wherein * represents the point of attachment to the iridium atom of the catalyst compound, and wherein ** represent the point of attachment to the imine-carbon atom to which the B ring is attached.

6. The catalyst compound of claim 1, wherein Z₁, Z₂, Z₃, Z₄, and Z₅ of the Formula I or Z₁, Z₂, Z₃, Z₄, and Z₅ of the Formula A are all methyl.

7. The catalyst compound of claim 1, wherein R₁ of the Formula I is hydrogen or methyl; or R₁ is (3C)alkylene linked to ring B to form a fused 6-membered ring, or R₁ of the Formula A is hydrogen or methyl, or R₁ is (3C)alkylene linked to ring B to form a fused 6-membered ring.

8. The catalyst compound of claim 1, wherein the catalyst compound is selected from any one of:

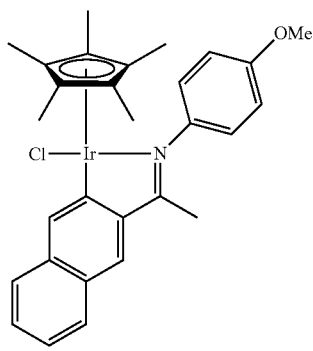

-continued

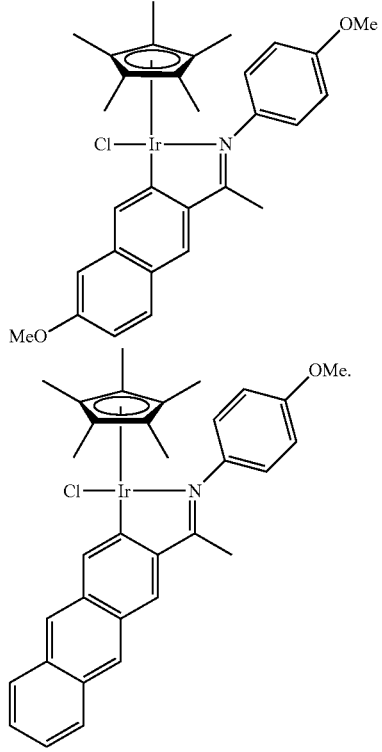

9. The catalyst compound of claim 1, wherein the catalyst compound has the structural formula:

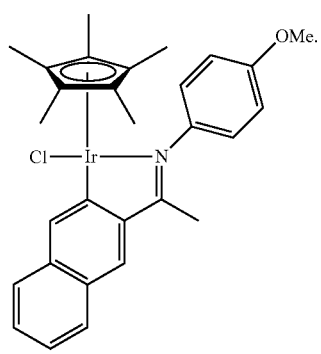

10. The catalyst compound of claim 1 as defined by Formula A, wherein ring B is phenyl optionally substituted, in either or both of the ortho- or para-position relative to the imine carbon atom to which ring B is attached, by (1-3C) alkoxy.

11. The catalyst compound of claim 1 as defined by Formula A, wherein R₁ is (3C)alkylene linked to ring B to form a fused 6-membered ring, optionally substituted as defined in claim 1.

12. The catalyst compound of claim 1 as defined by Formula A, wherein the catalyst compound is selected from:

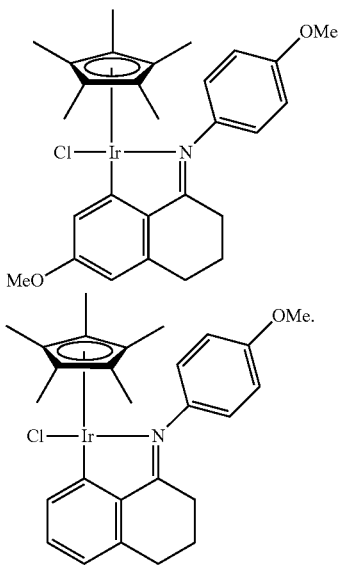

13. A method of reducing a reducible substrate, the method comprising hydrogenating the reducible substrate in the presence of a catalyst compound of Formula I

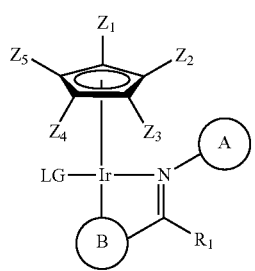

Formula I wherein:
ring A of the Formula I is aryl or heteroaryl, optionally substituted by one or two groups selected from the group consisting of hydroxyl, $NR^aR^b$, (1-6C)alkyl, (1-6C)alkoxy, and aryl which is optionally substituted by halogeno, hydroxyl, $NR^aR^b$, (1-6C)alkyl, or (1-6C)alkoxy, wherein $R^a$ and $R^b$ are each independently hydrogen or (1-6C)alkyl;

ring B of the Formula I is a bicyclic or tricyclic aromatic or heteroaromatic fused ring system, optionally substituted by one or more groups selected from the group consisting of halogeno, hydroxyl, $NR^cR^d$, (1-6C)alkyl, (1-6C)alkoxy, $[NR^cR^dR^e]^+$, nitro, cyano, formyl, carboxy, carbamoyl, sulphamoyl, ureido, isocyano, sulphonyl, sulphonate, trihalomethyl and mercapto, wherein $R^c$, $R^d$, and $R^e$ are each independently hydrogen, (1-6C)alkyl or aryl, or a group of the formula:

$L_1$-$Q_1$ wherein:
$L_1$ is absent or is selected from the group consisting of O, S, SO, $SO_2$, $N(R^f)$, C(O), $CH(OR^f)$, $C(O)N(R^f)$, $N(R^f)C(O)$, $N(R^f)C(O)N(R^g)$, $S(O)_2N(R^f)$, and $N(R^f)SO_2$, wherein $R^f$ and $R^g$ are each independently hydrogen or (1-4C)alkyl; and $Q_1$ is (1-6C)alkyl, (2-6C)alkenyl, (2-6C)alkynyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; wherein $Q_1$ is optionally further substituted by one or more substituents each independently selected from the group consisting of halogeno, hydroxyl, $NR^cR^d$, $[NR^cR^dR^e]^+$, (1-6C)alkyl, (1-6C)alkoxy, nitro, cyano, formyl, carboxy, carbamoyl, ureido, isocyano, sulphonyl, sulphonate, trifluoromethyl, and mercapto;

$R_1$ of the Formula I is selected from the group consisting of hydrogen, (1-6C)alkyl, (2-6C)alkenyl, (2-6C)alkynyl, aryl, (3-6C)cycloalkyl and heteroaryl; or $R_1$ is (2-4C)alkylene or (2-4C)alkenylene linked to ring B to form a fused 5-, 6- or 7-membered ring, wherein $R_1$ is optionally substituted by one or more groups selected from the group consisting of halogen, hydroxyl, $NR^hR^i$, (1-6C)alkyl, (1-6C)alkoxy, $[NR^hR^iR^j]^+$, nitro, cyano, formyl, carboxy, carbamoyl, sulphamoyl, ureido, isocyano, sulphonyl, sulphonate, trihalomethyl and mercapto, wherein $R^h$, $R^i$, and $R^j$ are each independently hydrogen, (1-6C)alkyl or aryl, or a group of the formula:

$L_2$-$Q_2$ wherein:
$L_2$ is absent or is selected from the group consisting of O, S, SO, $SO_2$, $N(R^k)$, C(O), $CH(OR^k)$, $C(O)N(R^k)$, $N(R^k)C(O)$, $N(R^k)C(O)N(R^l)$, $S(O)_2N(R^k)$, and $N(R^k)SO_2$, wherein $R^k$ and $R^l$ are each independently hydrogen or (1-4C)alkyl; and $Q_2$ is (1-6C)alkyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; wherein $Q_2$ is optionally further substituted by one or more substituents each independently selected from the group consisting of halogeno, hydroxyl, $NR^mR^n$, $[NR^mR^nR^o]^+$, (1-6C)alkyl, (1-6C)alkoxy, nitro, cyano, formyl, carboxy, carbamoyl, ureido, isocyano, sulphonyl, sulphonate, trifluoromethyl, and mercapto, wherein $R^m$, $R^n$, and $R^o$ are each independently hydrogen, (1-6C)alkyl or aryl;

LG of the Formula I is a leaving group;

$Z_1$, $Z_2$, $Z_3$, $Z_4$, and $Z_5$ of the Formula I are each independently selected from the group consisting of hydrogen, (1-6C)alkyl, aryl, (1-6C)alkoxy, hydroxyl, and $NR^pR^q$, wherein $R^p$ and $R^q$ are each independently hydrogen, (1-6C)alkyl or aryl, or in the presence of a catalyst compound of Formula A

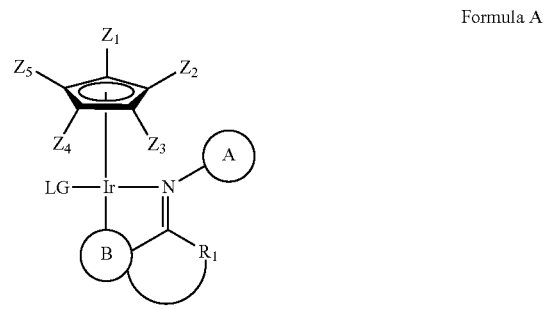

Formula A wherein:
ring A of the Formula A is aryl or heteroaryl, optionally substituted by one or two groups each independently selected from the group consisting of hydroxyl, $NR^aR^b$, (1-6C)alkyl, (1-6C)alkoxy, and aryl which is optionally substituted by halogeno, hydroxyl, $NR^aR^b$, (1-6C)alkyl or (1-6C)alkoxy, wherein $R^a$ and $R^b$ are each independently hydrogen or (1-6C)alkyl;

ring B of the Formula A is a aryl or heteroaryl, optionally substituted by one or more groups each independently selected from the group consisting of halogeno, hydroxyl, $NR^cR^d$, (1-6C)alkyl, (1-6C)alkoxy, $[NR^cR^dR^e]^+$, nitro, cyano, formyl, carboxy, carbamoyl, sulphamoyl, ureido, isocyano, sulphonyl, sulphonate, trihalomethyl and mercapto, wherein $R^c$, $R^d$, and $R^e$ are each independently hydrogen, (1-6C)alkyl or aryl, or a group of the formula:

$L_1$-$Q_1$ wherein:
$L_1$ is absent or is selected from the group consisting of O, S, SO, $SO_2$, $N(R^f)$, C(O), $CH(OR^f)$, $C(O)N(R^f)$, $N(R^f)C(O)$, $N(R^f)C(O)N(R^g)$, $S(O)_2N(R^f)$, and $N(R^f)SO_2$, wherein $R^f$ and $R^g$ are each independently hydrogen or (1-4C)alkyl; and $Q_1$ is (1-6C)alkyl, (2-6C)alkenyl, (2-6C)alkynyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; wherein $Q_1$ is optionally further substituted by one or more substituents each independently selected from the group consisting of halogeno, hydroxyl, $NR^cR^d$, $[NR^cR^dR^e]^+$, (1-6C)alkyl, (1-6C)alkoxy, nitro, cyano, formyl, carboxy, carbamoyl, ureido, isocyano, sulphonyl, sulphonate, trifluoromethyl and mercapto;

$R_1$ of the Formula A is (2-4C)alkylene or (2-4C)alkenylene linked to ring B to form a fused 5- 6-, or 7-membered ring, wherein $R_1$ is optionally substituted by one or more groups each independently selected from the group consisting of halogeno, hydroxyl, $NR^hR^i$, (1-6C)alkyl, (1-6C)alkoxy, $[NR^hR^iR^j]^+$, nitro, cyano, formyl, carboxy, carbamoyl, sulphamoyl, ureido, isocyano, sulphonyl, sulphonate, trihalomethyl and mercapto, wherein $R^h$, $R^i$, and $R^j$ are each independently hydrogen, (1-6C) alkyl or aryl, or a group of the formula:

$L_2$-$Q_2$ wherein:
$L_2$ is absent or is selected from the group consisting of O, S, SO, $SO_2$, $N(R^k)$, C(O), $CH(OR^k)$, $C(O)N(R^k)$, $N(R^k)C(O)$, $N(R^k)C(O)N(R^l)$, $S(O)_2N(R^k)$ and $N(R^k)SO_2$, wherein $R^k$ and $R^l$ are each independently hydrogen or (1-4C)alkyl; and $Q_2$ is (1-6C)alkyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; wherein $Q_2$ is optionally further substituted by one or more substituents each independently selected from the group consisting of halogeno, hydroxyl, $NR^mR^n$, $[NR^mR^nR^o]^+$, (1-6C)alkyl, (1-6C)alkoxy, nitro, cyano, formyl, carboxy, carbamoyl, ureido, isocyano, sulphonyl, sulphonate, trifluoromethyl; and mercapto, wherein $R^m$, $R^n$, and $R^o$ are each independently hydrogen, (1-6C)alkyl or aryl;

LG of the Formula A is a leaving group;

$Z_1$, $Z_2$, $Z_3$, $Z_4$, and $Z_5$ of the Formula A are each independently selected from the group consisting of hydrogen, (1-6C)alkyl, aryl, (1-6C)alkoxy, hydroxyl and $NR^pR^q$, wherein $R^p$ and $R^q$ are each independently hydrogen, (1-6C)alkyl or aryl.

14. The method of claim 13, wherein the reducible substrate comprises at least one reducible moiety, wherein the at least one reducible moiety comprises a polar π-bond.

15. The method of claim 14, wherein the at least one reducible moiety is selected from an imine and an iminium group, optionally an imine or iminium prepared in situ by a reaction between a ketone or an aldehyde and ammonia or an amine.

16. The method of claim 13, wherein hydrogenating the reducible substrate occurs via transfer hydrogenation, optionally wherein a hydrogen donor in the transfer hydrogenation comprises formic acid or formate.

17. The method of claim 13, wherein the hydrogenation solvent comprises a (2-3C)alcohol optionally substituted by one or more halides.

18. The method of claim 13, wherein the hydrogenation reaction mixture comprises at most 0.005 molar equivalents of the catalyst compound per molar equivalent of reducible moiety of the reducible substrate.

19. The method of claim 13, wherein the hydrogenation reaction is carried out at a temperature between 40° C. and 120° C.

20. A kit of parts comprising either:
the compound of Formula II:

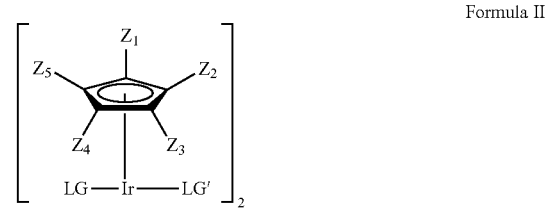

Formula II wherein $Z_1$, $Z_2$, $Z_3$, $Z_4$, $Z_5$ of the Formula II are each independently selected from the group consisting of hydrogen, (1-6C)alkyl, aryl, (1-6C)alkoxy, hydroxyl, and $NR^pR^q$, wherein $R^p$ and $R^q$ are each independently hydrogen, (1-6C)alkyl or aryl and LG of the Formula II is a leaving group, and LG' is a leaving group;

and the compound of Formula III:

Formula III wherein ring A of the Formula III is aryl or heteroaryl, optionally substituted by one or two groups selected from the group consisting of hydroxyl, $NR^aR^b$, (1-6C) alkyl, (1-6C)alkoxy, and aryl which is optionally substituted by halogeno, hydroxyl, $NR^aR^b$, (1-6C)alkyl, or (1-6C)alkoxy, wherein $R^a$ and $R^b$ are each independently hydrogen or (1-6C)alkyl;

ring B of the Formula III is a bicyclic or tricyclic aromatic or heteroaromatic fused ring system, optionally substituted by one or more groups selected from the group consisting of halogeno, hydroxyl, $NR^cR^d$, (1-6C)alkyl, (1-6C)alkoxy, $[NR^cR^dR^e]^+$, nitro, cyano, formyl, carboxy, carbamoyl, sulphamoyl, ureido, isocyano, sulphonyl, sulphonate, trihalomethyl and mercapto, wherein $R^c$, $R^d$, and $R^e$ are each independently hydrogen, (1-6C) alkyl or aryl, or a group of the formula:

$L_1$-$Q_1$ wherein:
$L_1$ is absent or is selected from the group consisting of O, S, SO, $SO_2$, $N(R^f)$, C(O), $CH(OR^f)$, $C(O)N(R^f)$, $N(R^f)C(O)$, $N(R^f)C(O)N(R^g)$, $S(O)_2N(R^f)$, and $N(R^f)SO_2$, wherein $R^f$ and $R^g$ are each independently hydrogen or (1-4C)alkyl; and $Q_1$ is (1-6C)alkyl, (2-6C)alkenyl, (2-6C)alkynyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; wherein $Q_1$ is optionally further substituted by one or more substituents each independently selected from the group consisting of halogeno, hydroxyl, $NR^cR^d$, $[NR^cR^dR^e]^+$, (1-6C)alkyl, (1-6C)alkoxy, nitro, cyano, formyl, carboxy, carbamoyl, ureido, isocyano, sulphonyl, sulphonate, trifluoromethyl, and mercapto; and $R_1$ of the Formula III is selected from the group consisting of hydrogen, (1-6C)alkyl, (2-6C)alkenyl, (2-6C)alkynyl, aryl, (3-6C)cycloalkyl and heteroaryl; or $R_1$ is (2-4C)alkylene or (2-4C)alkenylene linked to ring B to form a fused 5-, 6- or 7-membered ring, wherein $R_1$ is optionally substituted by one or more groups selected from the group consisting of halogeno, hydroxyl, $NR^hR^i$, (1-6C)alkyl, (1-6C)alkoxy, $[NR^hR^iR^j]^+$, nitro, cyano, formyl, carboxy, carbamoyl, sulphamoyl, ureido, isocyano, sulphonyl, sulphonate, trihalomethyl and mercapto, wherein $R^h$, $R^i$, and $R^j$ are each independently hydrogen, (1-6C)alkyl or aryl, or a group of the formula:

$L_2$-$Q_2$ wherein:
$L_2$ is absent or is selected from the group consisting of O, S, SO, $SO_2$, $N(R^k)$, C(O), $CH(OR^k)$, $C(O)N(R^k)$, $N(R^k)C(O)$, $N(R^k)C(O)N(R^l)$, $S(O)_2N(R^k)$, and $N(R^k)SO_2$, wherein $R^k$ and $R^l$ are each independently hydrogen or (1-4C)alkyl; and $Q_2$ is (1-6C)alkyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; wherein $Q_2$ is optionally further substituted by one or more substituents each independently selected from the group consisting of halogeno, hydroxyl, $NR^mR^n$, $[NR^mR^nR^o]^+$, (1-6C)alkyl, (1-6C)alkoxy, nitro, cyano, formyl, carboxy, carbamoyl, ureido, isocyano, sulphonyl, sulphonate, trifluoromethyl, and mercapto, wherein $R^m$, $R^n$, and $R^o$ are each independently hydrogen, (1-6C)alkyl or aryl;

LG of the Formula I is a leaving group;
$Z_1$, $Z_2$, $Z_3$, $Z_4$, and $Z_5$ of the Formula I are each independently selected from the group consisting of hydrogen, (1-6C)alkyl, aryl, (1-6C)alkoxy, hydroxyl, and $NR^pR^q$, wherein $R^p$ and $R^q$ are each independently hydrogen, (1-6C)alkyl or aryl;

or
the compound of Formula II:

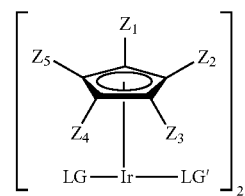

Formula II wherein $Z_1$, $Z_2$, $Z_3$, $Z_4$, $Z_5$ of the Formula II are each independently selected from the group consisting of hydrogen, (1-6C)alkyl, aryl, (1-6C)alkoxy, hydroxyl, and $NR^pR^q$, wherein $R^p$ and $R^q$ are each independently hydrogen, (1-6C)alkyl or aryl and LG of the Formula II is a leaving group, and LG' is a leaving group;

and the compound of Formula B:

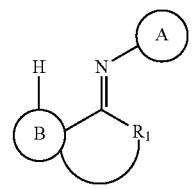

Formula B wherein ring A of the Formula B is aryl or heteroaryl, optionally substituted by one or two groups each independently selected from the group consisting of hydroxyl, $NR^aR^b$, (1-6C)alkyl, (1-6C)alkoxy, and aryl which is optionally substituted by halogeno, hydroxyl, $NR^aR^b$, (1-6C)alkyl or (1-6C)alkoxy, wherein $R^a$ and $R^b$ are each independently hydrogen or (1-6C)alkyl;

ring B of the Formula B is a aryl or heteroaryl, optionally substituted by one or more groups each independently selected from the group consisting of halogeno, hydroxyl, $NR^cR^d$, (1-6C)alkyl, (1-6C)alkoxy, $[NR^cR^dR^e]^+$, nitro, cyano, formyl, carboxy, carbamoyl, sulphamoyl, ureido, isocyano, sulphonyl, sulphonate, trihalomethyl and mercapto, wherein $R^c$, $R^d$, and $R^e$ are each independently hydrogen, (1-6C)alkyl or aryl, or a group of the formula:

$L_1$-$Q_1$ wherein:
$L_1$ is absent or is selected from the group consisting of O, S, SO, $SO_2$, $N(R^f)$, C(O), $CH(OR^f)$, $C(O)N(R^f)$, $N(R^f)C(O)$, $N(R^f)C(O)N(R^g)$, $S(O)_2N(R^f)$, and $N(R^f)SO_2$, wherein $R^f$ and $R^g$ are each independently hydrogen or (1-4C)alkyl; and $Q_1$ is (1-6C)alkyl, (2-6C)alkenyl, (2-6C)alkynyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; wherein $Q_1$ is optionally further substituted by one or more substituents each independently selected from the group consisting of halogeno, hydroxyl, $NR^cR^d$, $[NR^cR^dR^e]^+$, (1-6C)alkyl, (1-6C)alkoxy, nitro, cyano, formyl, carboxy, carbamoyl, ureido, isocyano, sulphonyl, sulphonate, trifluoromethyl and mercapto; and $R_1$ of the Formula B is (2-4C)alkylene or (2-4C)alkenylene linked to ring B to form a fused 5- 6-, or 7-membered ring, wherein $R_1$ is optionally substituted by one or more groups each independently selected from the group consisting of halogeno, hydroxyl, $NR^hR^i$, (1-6C)alkyl, (1-6C)alkoxy, $[NR^hR^iR^j]^+$, nitro, cyano, formyl, carboxy, carbamoyl, sulphamoyl, ureido, isocyano, sulphonyl, sulphonate, trihalomethyl and mercapto, wherein $R^h$, $R^i$, and $R^j$ are each independently hydrogen, (1-6C)alkyl or aryl, or a group of the formula:

$L_2$-$Q_2$ wherein:
$L_2$ is absent or is selected from the group consisting of O, S, SO, $SO_2$, $N(R^k)$, C(O), $CH(OR^k)$, $C(O)N(R^k)$, $N(R^k)C(O)$, $N(R^k)C(O)N(R^l)$, $S(O)_2N(R^k)$ and $N(R^k)SO_2$, wherein $R^k$ and $R^l$ are each independently hydrogen or (1-4C)alkyl; and
$Q_2$ is (1-6C)alkyl, aryl, aryl-(1-6C)alkyl, (3-6C)cycloalkyl, (3-6C)cycloalkyl-(1-6C)alkyl, (3-6C)cycloalkenyl, (3-6C)cycloalkenyl-(1-6C)alkyl, heteroaryl, heteroaryl-(1-6C)alkyl, heterocyclyl or heterocyclyl-(1-6C)alkyl; wherein $Q_2$ is optionally further substituted by one or more substituents each independently selected from the group consisting of halogeno, hydroxyl, $NR'''R''$, $[NR'''R''R^o]^+$, (1-6C)alkyl, (1-6C)alkoxy, nitro, cyano, formyl, carboxy, carbamoyl, ureido, isocyano, sulphonyl, sulphonate, trifluoromethyl and mercapto, wherein $R'''$, $R''$, and $R^o$ are each independently hydrogen, (1-6C)alkyl or aryl.

\* \* \* \* \*